(12) United States Patent
Bjørnerud et al.

(10) Patent No.: US 8,718,747 B2
(45) Date of Patent: May 6, 2014

(54) ESTIMATING AND CORRECTING FOR CONTRAST AGENT EXTRAVASATION IN TISSUE PERFUSION IMAGING

(75) Inventors: Atle Bjørnerud, Oslo (NO); Kyrre Eeg Emblem, Cambridge, MA (US)

(73) Assignee: Oslo Universitetssykehus HF, Oslo (NO)

( * ) Notice: Subject to any disclaimer, the term of this patent is extended or adjusted under 35 U.S.C. 154(b) by 196 days.

(21) Appl. No.: 13/088,972

(22) Filed: Apr. 18, 2011

(65) Prior Publication Data
US 2011/0257519 A1 Oct. 20, 2011

Related U.S. Application Data

(60) Provisional application No. 61/325,019, filed on Apr. 16, 2010.

(51) Int. Cl.
*A61B 6/00* (2006.01)
(52) U.S. Cl.
USPC ........... 600/431; 600/420; 600/410; 600/416; 382/128; 382/131
(58) Field of Classification Search
USPC ................... 702/19; 600/420, 504, 410, 416; 382/128, 131; 424/9.3
See application file for complete search history.

(56) References Cited

U.S. PATENT DOCUMENTS

| 6,542,769 | B2 * | 4/2003 | Schwamm et al. | 600/420 |
|---|---|---|---|---|
| 6,807,441 | B2 * | 10/2004 | Schmainda | 600/424 |
| 7,069,068 | B1 * | 6/2006 | Ostergaard | 600/420 |
| 7,512,435 | B2 * | 3/2009 | Wu et al. | 600/431 |
| 7,567,832 | B2 * | 7/2009 | Schmainda et al. | 600/410 |
| 8,285,490 | B2 * | 10/2012 | Yang | 702/19 |
| 8,326,400 | B2 * | 12/2012 | Taxt et al. | 600/420 |
| 2002/0111550 | A1 * | 8/2002 | Schwamm et al. | 600/419 |
| 2004/0218794 | A1 * | 11/2004 | Kao et al. | 382/128 |
| 2005/0187462 | A1 * | 8/2005 | Koh et al. | 600/416 |
| 2006/0034765 | A1 * | 2/2006 | Schmainda et al. | 424/9.3 |

(Continued)

OTHER PUBLICATIONS

Bjornerud et al, "T1- and T2*-dominant extravasation correction in DSC-MRI: Part I—theoretical considerations and implications for assessment of tumor hemodynamic properties", Journal of Cerebral Blood Flow & Metabolism (2011), 31, 2041-2053.*

(Continued)

*Primary Examiner* — Long V. Le
*Assistant Examiner* — Nicholas Evoy
(74) *Attorney, Agent, or Firm* — Knobbe Martens Olson & Bear LLP

(57) ABSTRACT

The invention provides a method, an image analysis software product, and a system for medical imaging analysis for estimating contrast agent extravasation in contrast agent based perfusion imaging such as MRI dynamic contrast enhanced (DCE) imaging, and in particular correction, compensation, or visualization of extravascular leakage of contrast agent in tumors. According to the invention, the effect of extravasation is directly manifested in the tail part of an observed, apparent residue function, R'(t), obtained directly by de-convoluting the expression $C(t)=R'(t) \otimes C_p'(t)$ with the arterial input function (AIF). A leakage rate or extravasation constant is determined directly from the tail part of the determined apparent residue function. The invention also relates to distinguishing between $T_1$-dominant and $T_2^*$-dominant extravasation effects in perfusion imaging to from the sign of the tail part of the determined apparent residue function and to an automated method for DSC-MRI involving correction for contrast agent extravasation and partial volume effects.

13 Claims, 13 Drawing Sheets

(56) References Cited

U.S. PATENT DOCUMENTS

| | | | |
|---|---|---|---|
| 2006/0083687 A1* | 4/2006 | Yang | 424/9.3 |
| 2007/0112264 A1* | 5/2007 | Wu et al. | 600/410 |
| 2007/0167731 A1* | 7/2007 | Taxt et al. | 600/410 |
| 2011/0118615 A1* | 5/2011 | Yang | 600/504 |
| 2012/0141005 A1* | 6/2012 | Djeridane et al. | 382/131 |

OTHER PUBLICATIONS

Boxerman et al, "Relative Cerebral Blood Volume Maps Corrected for Contrast Agent Extravasation Significantly Correlate with Glioma Tumor Grade, Whereas Uncorrected Maps Do Not", AJNR Am J Neuroradiol 27:859-67, Apr. 2006.*

Brix et al, "Microcirculation and Microvasculature in Breast Tumors: Pharmacokinetic Analysis of Dynamic MR Image Series", Magnetic Resonance in Medicine 52: 420-429 (2004).*

Goldstein et al, "Fast Mapping of Myocardial Blood Flow with Mr First-Pass Perfusion Imaging", Magnetic Resonance in Medicine 59: 1394-1400 (2008).*

Koh et al, "Cerebral perfusion mapping using a robust and efficient method for deconvolution analysis of dynamic contrast-enhanced images", NeuroImage 32 (2006) 643-653.*

Quarles et al, "Improving the Reliability of Obtaining Tumor Hemodynamic Parameters in the Presence of Contrast Agent Extravasation", Magnetic Resonance in Medicine 53: 1307-1316 (2005).*

Sakoglu et al, "Cerebral blood flow estimation from perfusion-weighted MRI using FT-based MMSE filtering method", Magnetic Resonance Imaging 26 (2008) 313-322.*

Bjornerud, Atle et al., "$T_1$-and $T_2$*- Dominant Extravasation Correction in DSC-MRI: Part I—Theoretical Considerations and Implications for Assessment of Tumor Hemodynamic Properties" Journal of Cerebral Blood Flow & Metabolism, pp. 1-39.

Boxerman, J.L. et al., "Relative Cerebral Blood Volume Maps Corrected for Contrast Agent Extravasation Significantly Correlate with Glioma Tumor Grade, Whereas Uncorrected Maps Do Not" AJNR Am J Neuroradiol, Apr. 2006, pp. 859-867, vol. 27.

Mouridsen, Kim et al., "Automatic Selection of Arterial Input Function Using Cluster Analysis" Magnetic Resonance in Medicine, 2006, pp. 524-531, vol. 55.

Quarles, C. C. et al., "Improving the Reliability of Obtaining Tumor Hemodynamic Parameters in the Presence of Contrast Agent Extravasation" Magnetic Resonance in Medicine, 2005, pp. 1307-1316, vol. 53.

* cited by examiner

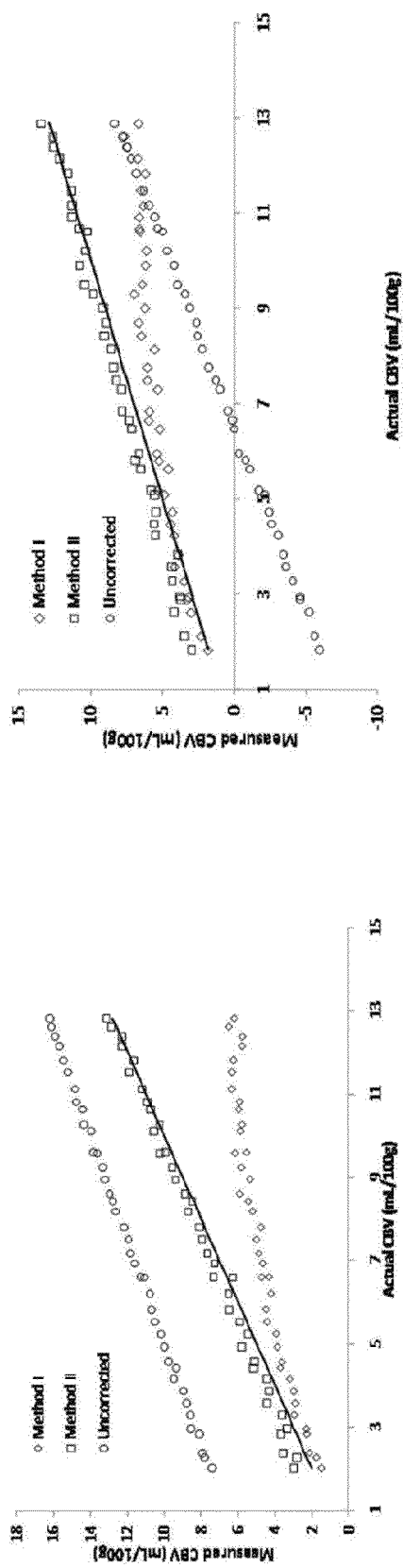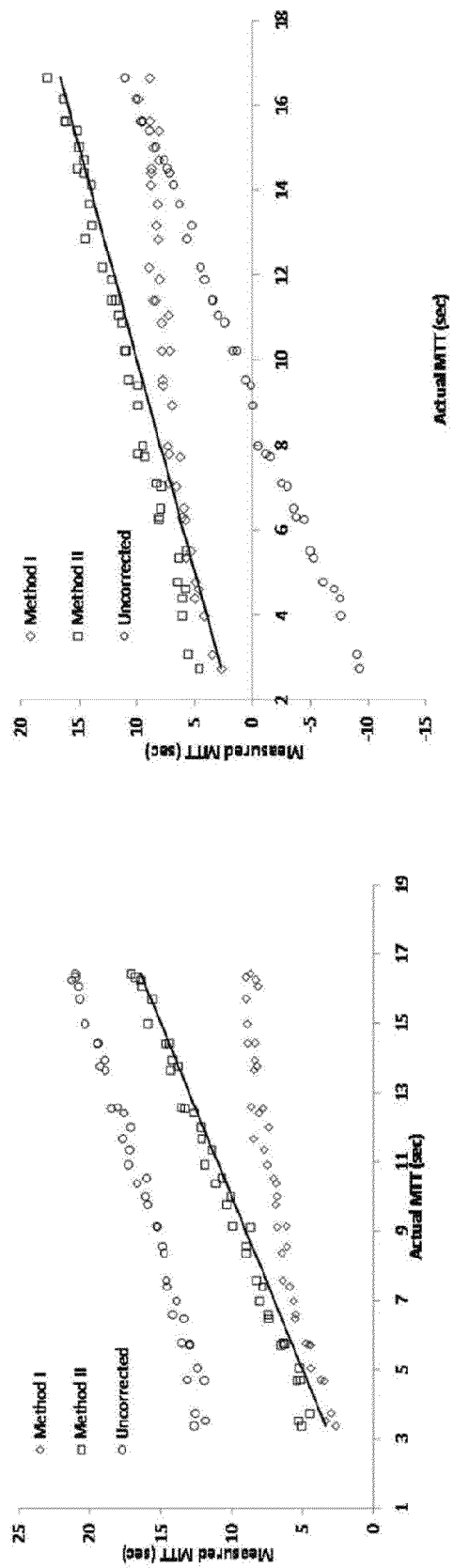
Fig. 7A
Fig. 7B

ESTIMATING AND CORRECTING FOR CONTRAST AGENT EXTRAVASATION IN TISSUE PERFUSION IMAGING

CROSS REFERENCE TO RELATED APPLICATIONS

This application is a non-provisional of and claims the benefit of priority to U.S. provisional Patent Application Ser. No. 61/325,019, filed on Apr. 16, 2010, the disclosures of which are hereby expressly incorporated by reference in their entireties.

FIELD OF THE INVENTION

The present invention relates to perfusion analysis based on dynamic contrast enhanced (DCE) imaging, in particular correction or compensation due to extravascular leakage of the contrast agent in tumors.

BACKGROUND OF THE INVENTION

In DCE imaging, an MRI or CT sequence is recorded after a contrast agent (CA) has been injected intravenously. The recorded sequence consist of dynamic concentration time curves (CTC) recorded for each voxel, which shows the contrast agent induced signal (~which can be related to relative CA concentration) in a given voxel as a function of time. Thereby, DCE imaging can be used to make a quantitative estimates of tissue perfusion and tissue blood volume, i.e. the amount of blood per unit tissue volume and per unit time that flow through the capillaries of the vascular bed of a given tissue region. These quantitative estimates of tissue perfusion metric can reveal details related the type and state of the tissue, also referred to herein as hemodynamic parameters. In particular, dynamic susceptibility contrast (DSC) MRI is an increasingly used method to characterize brain tumors and in particular gliomas. Several studies have shown that DSC-MRI can be used to improve tumor grading and further to predict patient prognosis and treatment response.

However, a number of artefacts appear in DCE imaging, two of which are the subject of the present invention.

An important step in quantitative tumor perfusion analysis is related to correction for extravascular leakage of the contrast agent into the tumor tissue. Many brain tumors result in disrupted blood-brain-barrier (BBB) causing the contrast agent to leave the intravascular space and leak into the interstitial space. This extravasation has a confounding effect on the estimations of tumor blood volume and perfusion unless corrected for One particular mathematical correction method has become widely used is described in Boxerman et al., American Journal of Neuroradiology 27 (2006), 859-67 as well as in U.S. Pat. No. 6,807,441. The method suggested herein corrects for extravasation by assuming relaxation to be dominated by $T_1$-shortening and then correct for leakage relative to an average first-pass pass response for the entire image slice. The method implicitly assumes that the variation in tissue MTT and delay is small relative to the slice average MTT/delay. Given the highly heterogeneous vasculature in tumor such as gliomas, MTT/delay values which deviate significantly from the mean MTT are very likely and may lead to incorrect estimations of contrast agent extravasation. This method is used as a reference method and is denoted Method I in the following.

Another method described in U.S. Pat. No. 7,567,832 and Quarles et al., Magnetic Resonance in Medicine 53 (2005), 1307-1316. A disadvantage of this approach is that a very long time series is needed to correctly identify the leakage term from the apparent residue function and further that CBV leakage correction cannot be performed directly from the residue function.

Hence, improved ways of estimating and correcting for extravascular leakage of contrast agent would be advantageous.

SUMMARY OF THE INVENTION

It is an object of the present invention to provide an improved procedure for estimating extravasation rates and/or correcting extravascular leakage of contrast agent in contrast agent based perfusion imaging such as DCE MRI and CT imaging.

It is another object of the present invention to provide a method for estimating contrast agent extravasation in contrast agent based perfusion imaging such as MRI dynamic contrast enhanced (DCE) imaging that solves the above mentioned problems of the prior art with correction of extravascular leakage of the contrast agent.

It is a further object to provide a method, a computer program and a system for correction of contrast agent extravasation.

Further objects relate to a method of distinguishing between $T_1$-dominant and $T_2^*$-dominant extravasation effects in perfusion imaging and an automated method for DSC-MRI involving correction for contrast agent extravasation and partial volume effects.

In the prior art, it is customary to represent the measured contrast agent concentration, C(t), in the absence of extravasation as a result of a convolution between the concentration time curve in an artery feeding the tissue of interest, $C_p(t)$ (the arterial input function, AIF) and a residue function; R(t) so that $C(t)=F \cdot R(t) \otimes C_p(t)$, where R(t) describes the fraction of injected contrast agent still present in a tissue voxel at time t and F is tissue perfusion. In the mathematical analysis used to estimate perfusion, the perfusion scaled residue function $R_{ps}(t)=FR(t)$ can be estimated and perfusion is then given by the value of $R_{ps}(t)$ at t=0.

To take leakage into consideration, two different methods have been proposed in the prior art. In Method I (U.S. Pat. No. 6,807,441 and Boxerman et al), extravasation is estimated by comparing the tissue response curve averaged for all brain voxels without leakage (identified by certain a priori assumptions about the shape of C(t) in the absence of leakage) with the tissue response in any given voxel. Any deviation in the shape of C(t) for a given voxel relative to the mean C(t) is then assumed to be due to extravasation. From this, the relative extravasation rate constant can then be estimated by applying an appropriate kinetic model. This method implicitly assumes that any deviation in shape of C(t) is only due to extravasation effects. However, variations in tissue transit times or delay times may also result in deviations in the shape of C(t) relative to the mean curve, and this would then be misinterpreted as extravasation.

In a modified correction method (U.S. Pat. No. 7,567,832 and Quarles et al.), the leakage constant is estimated from the tissue residue function directly by making certain (strict) assumptions about the properties of the leakage effect. The estimated leakage constant is then back-substituted into the expression used in Method I to obtain corrected CBV values. The advantage of this method is that the resulting leakage constant is not affected by deviations in tissue transit times. The disadvantage of this method is that the resulting estimation of the leakage constant is very sensitive to the underlying mathematical methods used to derive the residue function and will only give correct estimates for very long time series. Further, the method must be combined with method I to obtain corrected CBV values.

$C_p(t)$ may e.g. be estimated from the signal in voxels only containing plasma such as large arteries. It is noted, that estimation of $C_p(t)$ (or AIF) is an entire field in itself, and that several techniques for this are well known to the skilled person, see e.g. Mouridsen et al., Automatic Selection of Arterial Input Function Using Cluster Analysis, Magnetic Resonance in Medicine 55:524-531 (2006). The leakage correction procedure present invention involves the advantage that it is not critically dependent on which technique is applied for estimating $C_p(t)$.

In the present invention, the extravasation constant is also estimated directly from the residue function which makes the method insensitive to variations in mean transit times. However, different from the prior art, the leakage constant is estimated directly from curve fitting of the resulting in an observed, leakage-affected residue function, referred to as the apparent residue function R'(t), without including the leakage term as an explicit parameter in the mathematical model used to derive R(t). This has the advantage of making the estimation of R'(t) more robust with less restrictions on the underlying kinetic model and also, after the leakage constant is estimated from R'(t), a leakage corrected residue function can be estimated and from this leakage corrected CBV can be determined directly without the need to re-generate tissue response curves.

It is thus assumed that that the effect of extravasation can be directly accounted for in the apparent residue function and that extravasation correction of the acquired signal is therefore not necessary prior to deconvolution with the estimated $C'_p(t)$. The apparent residue function R'(t), like the ideal residue function R(t), has an initial peak or maximum followed by a decaying "tail", which is a result of the contrast agent kinetics can be separated into two distinct hemodynamic phases. The present invention is based upon the realisation that the effect of extravasation is directly manifested in the tail part of the observed residue function which would be expected to have a zero asymptote in the absence of extravasation. The initial portion of the apparent residue function describes the intravascular effect of the contrast agent during the capillary passage whereas the later phase of the apparent residue function reflects the degree of extravasation of the agent from the intravascular space (IVS) to the extravascular extracellular space (EES) (and the reflux from EES to IVS). According to the invention, a first leakage rate constant $K_a$ (also referred to as K' in previous version of this application) quantifying an apparent rate of contrast agent extravasation from plasma (IVS) to extravascular, extracellular space (EES) is estimated directly from a tail part of the apparent residue function.

Typically, the signal is recorded during consecutive passages of the contrast agent through the vascular system, until the signal becomes very weak. In order to contain data representing the tail part of the apparent residue function, the signal should at least be recorded from before the first passage and until significant extravasation has occurred.

The invention proposes an alternative methodology for correction of contrast agent extravasation effects. According hereto, a leakage rate constant $K_a$ can be estimated directly from the deconvolution procedure. This provides the advantage of giving a more correct estimate of the mean transit time (MTT) in the presence of extravasation and also a more correct estimate of cerebral blood volume (CBV) in regions with altered MTT and/or contrast agent delay combined with significant extravasation effects. Further, the inventors have previously shown that CBV can be accurately determined directly from the tissue residue function in non-leaky tissue (see Bjornerud et al., A fully automated method for quantitative cerebral hemodynamic analysis using DSC-MRI. *J Cereb Blood Flow Metab* 30:1066-1078.), and by direct extravasation correction of the residue function according to an embodiment of the invention, the same method can be used to estimated leakage corrected CBV.

Thus, in a first aspect, the invention provides a method for estimating contrast agent extravasation in contrast agent based perfusion imaging in accordance with claim 1.

In a second aspect, the invention provides a method of distinguishing between $T_1$-dominant and $T_2^*$-dominant extravasation effects in perfusion imaging to from the sign of the tail part of the determined apparent residue function and producing maps or images visualizing the dominant extravasation effect. The method comprises the following steps to be performed by an electronic processor:

accessing perfusion image data comprising a signal related to contrast agent concentration as a function of time in a voxel during the first and consecutive passages of the contrast agent through the vascular system;

representing the signal by a convolution, $R_{ps}'(t) \otimes C_p'(t)$, of an apparent residue function, $R_{ps}'(t)$, and an estimated contrast agent concentration in plasma, $C_p'(t)$, and determining the apparent residue function $R_{ps}'(t)$ by deconvolution of the signal with $C_p'$;

determining a sign of the tail part of the apparent residue function; and generating an image of a parameter reflecting at least the determined sign and preferably also a magnitude of the tail part.

In a third aspect, the invention provides an automated method for DSC-MRI involving correction for contrast agent extravasation and partial volume.

In a fourth aspect, the invention provides a method for producing an image of contrast agent extravasation corrected hemodynamic parameter values with a medical imaging system.

In a fifth aspect, the invention provides an image analysis software for contrast agent based perfusion images, the image analysis software comprising a module for estimating contrast agent extravasation in contrast agent based perfusion image data.

In a sixth aspect, the invention provides a system for medical imaging analysis.

In the following description of the invention, a number of embodiments and preferred and/or optional features, elements, examples and implementations will be described. Features or elements described in relation to one embodiment, implementation or aspect may be combined with or applied to the other embodiments, implementations or aspects where applicable. For example, features applied in relation to a method may also be used as features in relation to software or a system and vice versa. Also, explanations of underlying mechanisms of the invention as realized by the inventors are presented for explanatory purposes, and should not be used in ex post facto analysis for deducing the invention.

$K_a$ is similar to, but not identical to $K^{trans}$. $K^{trans}$ quantifies the rate of contrast agent extravasation from plasma to extravascular, extracellular space (EES) when calculated in absolute quantitative terms (in units of mL/100 g/min). As will be described later, contrast agent extravasation artefacts results from a combination of both $T_1$ and $T_2^*$ effects so that a signal change cannot be directly related to CA concentration. $K_a$ therefore quantifies an apparent rate of contrast agent extravasation, and can substitute $K^{trans}$ in equations and algorithms for hemodynamic parameters.

The tissue residue function is the fraction of contrast agent concentration at time t (for the case of an ideal instantaneous bolus injected at t=0). However, since a large number of distortions and other effects are present, this strictly theoretical definition is mainly used in mathematical modelling. When performing practical calculations on real data, several other residue functions are relied upon. In the present description, the following terminology is used:

R(t) Tissue residue function, the fraction of contrast agent concentration at time t for the case of an ideal instantaneous bolus injected at t=0.

$R_{ps}(t)$ Perfusion scaled residue function, $R_{ps}(t)$=FR(t), where F=tissue perfusion or flow. This is the parameter that is commonly estimated by mathematical deconvolution of C(t) with $C_p(t)$, and the tissue response and perfusion is then given by the amplitude of $R_{ps}(t)$ at t=0 (or the peak amplitude with t>0 in case of delay effects). In previous version of this application, no explicit difference between whether the residue function was perfusion scaled or not was made.

$R_{ps}'(t)$ Perfusion scaled apparent residue function, the observed tissue residue function scaled by tissue flow and influenced by contrast agent extravasation and other distortions. This is what is determined from deconvolution of the measured C(t) with $C_p'(t)$ (AIF) in accordance with the invention. Is also referred to by R'(t) in cases where flow/perfusion scaling is implicit.

R'(t) Apparent tissue residue function, the tissue residue function influenced by contrast agent extravasation and other distortions; determined by R'(t)=$R_{ps}'(t)$/F. As the perfusion scaling is often implied, the term apparent residue function and the notation R'(t) are used to refer to both R'(t) and $R_{ps}'(t)$ in the present description unless explicit distinction is made.

$R_{corr}(t)$ Leakage corrected tissue residue function, determined from R'(t) or $R_{ps}'(t)$ and $K_a$.

In embodiments of the various aspects, it is preferred that an extravasation corrected residue function, $R_{corr}(t)$, is determined from the apparent residue function R'(t) and the estimated $K_a$. Then, using the first leakage rate constant $K_a$ or the extravasation corrected residue function $R_{corr}(t)$, extravasation corrected hemodynamic parameters may preferably be estimated for each voxel, such as one or more of: an extravasation-corrected CBV value, an extravasation-corrected mean transit time (MTT), and an extravasation-corrected bolus delay ($T_{max}$). Such extravasation-corrected CBV value will reflect the true intravascular volume and is unaffected by contrast agent extravasation.

Additionally, the proposed method allows for correction of both $T_1$- and $T_2^*$-dominant leakage effects. Here, $T_1$-dominant leakage effect refers to the situation where the CA results in a signal increase ($T_1$-shortening) after extravasation whereas $T_2^*$-dominant leakage refers to the situation where the CA results in a signal reduction ($T_2$- or $T_2^*$ shortening) after extravasation. Both effects can occur in brain tumors following extravasation depending on many factors both related to the underlying tumor microstructure as well as properties of the MR sequence used to generate the DSC-MRI data. It may therefore be preferred that $K_a$ is allowed to take both positive and negative values, and that the invention further comprises separating between $T_1$- and $T_2^*$-dominant leakage by determining the sign of $K_a$, so that negative $K_a$ values reflect $T_1$-dominant leakage effects and positive $K_a$ values reflect $T_2^*$-dominant leakage effects. In a preferred embodiment, this distinguishing between $T_1$-dominant and $T_2^*$-dominant extravasation effects is utilized to produce maps or images visualizing the dominant extravasation effect by imaging of e.g. the sign of the tail part of the apparent residue function (Sign|R'(t>>$T_c$)|), $K_a$, the sign of $K_a$, or similar.

In preferred embodiments, the imaged tissue is (preferably automatically) segmented into a tumor region and white and/or grey matter, and a mean value of $K_a$ are estimated for the tumor region.

The various aspects of the invention may be used to obtain quantitative assessment of multiple hemodynamic parameters in tumors, such as tumor classification, detection of malignant transformations; monitoring of therapy response, estimation of survival, and longitudinal monitoring.

In the present description, the signal related to contrast agent concentration as a function of time in voxels may be a change in amplitude of a contrast agent induced signal as recorded by a medical imaging apparatus such as an MR or CT scanner, or any signal derived there from. The intensity change is to be interpreted broadly and may e.g. be in the form of a relaxation rate or relative contrast agent concentration. Preferably, the signal is a concentration time curve (CTC). In one embodiment, the medical imaging apparatus is preferably an MR apparatus and the perfusion image data is recorded in a $T_2$ or $T_2^*$ weighed sequence. Alternatively or additionally, the perfusion data may include $T_1$ weighed sequence.

References to tumors are to be understood as a general reference to the following types: intra-axial brain tumors (e.g. gliomas), mammary tumors, prostate tumors, head and neck tumors, and intracranial metastasis, unless explicitly specified that the context in question. However, in preferred embodiments, the various aspects of the inventions are limited to intra-axial brain tumors, such as intra-axial primary brain tumors, preferably gliomas.

Embodiments of the various aspects of the invention relates to image analysis software, typically implemented as a computer program product. Such computer program product is adapted to enable a computer system comprising at least one computer having data storage means associated therewith to carry out the invention. Such a computer program product may be provided on any kind of computer readable medium, e.g. magnetically or optically based medium, or through a computer based network, e.g. the Internet.

The basic idea of the invention is to estimate extravasation rates or constants to be used in correcting for extravascular leakage by a new approximation of a tail part of an apparent tissue residue function accounting for the loss of contrast agent from the intravascular space (corresponding to the leakage of contrast agent into tissue).

BRIEF DESCRIPTION OF THE FIGURES

FIG. 5A shows AIFs automatically detected in each slice and FIG. 5B shows the corresponding average AIF across all slices together with the average venous output function (VOF). Gamma variate fitted curves are used to determine the steady-state portion and the PV correction factor is determined from the difference in the steady state levels of the AIF and VOF, respectively.

FIGS. 7A and B show the correlations between the estimated CBV and MTT after extravasation correction using the two correction methods compared to actual- and uncorrected values.

DETAILED DESCRIPTION OF AN EMBODIMENT

Figure 1:
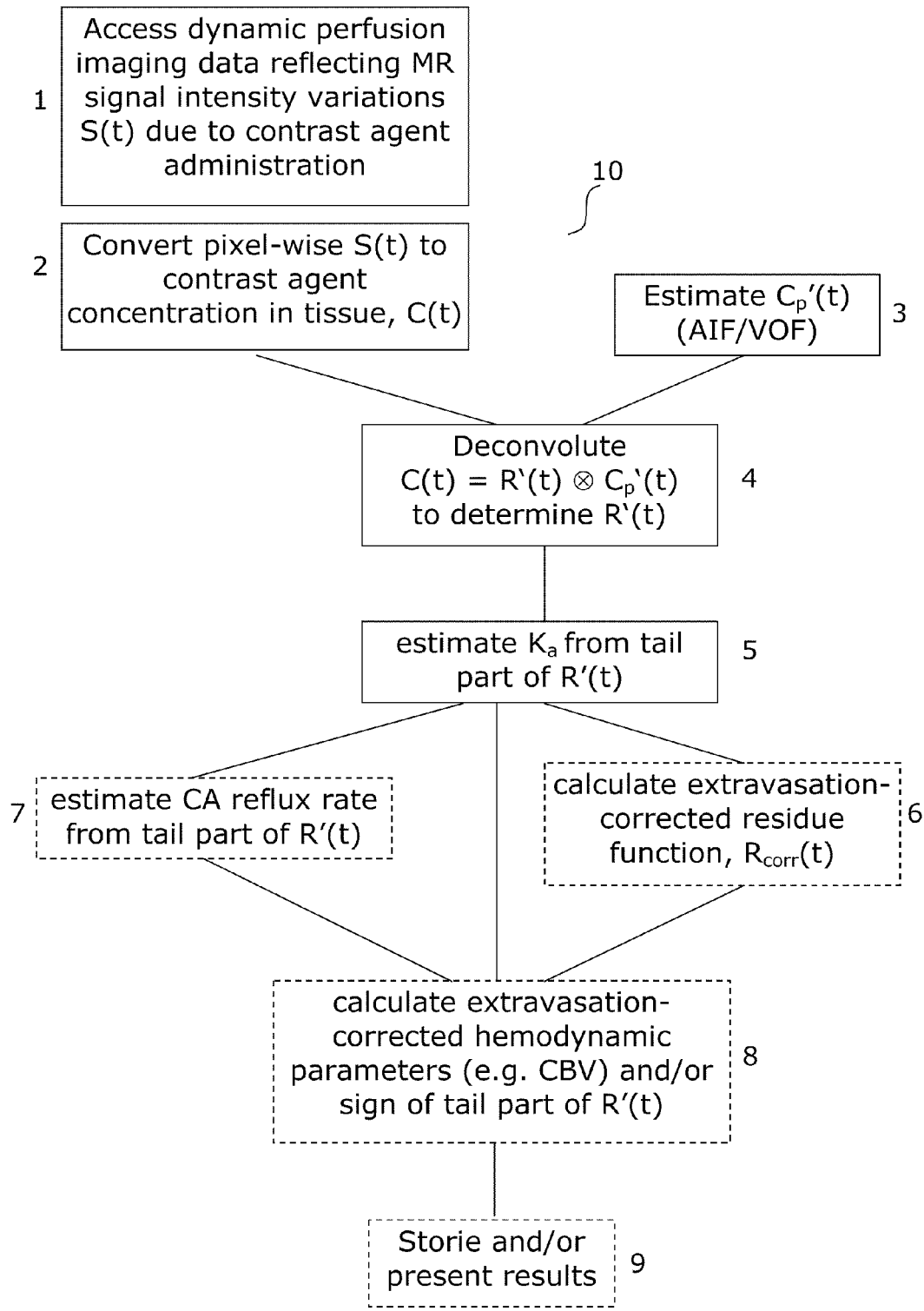
FIG. 1 is a flow diagram embodying the methods for correcting perfusion image data and the software applications according to various aspects of the invention.

The generalized flow diagram of FIG. 1 embodies the methods for correcting perfusion image data according to the various aspects of the invention. FIG. 1 further embodies the layout of software applications according to the various aspects of the invention.

The invention can be implemented by means of hardware, software, firmware or any combination of these. The invention or some of the features thereof can also be implemented as software running on one or more data processors and/or digital signal processors.

Figure 2:
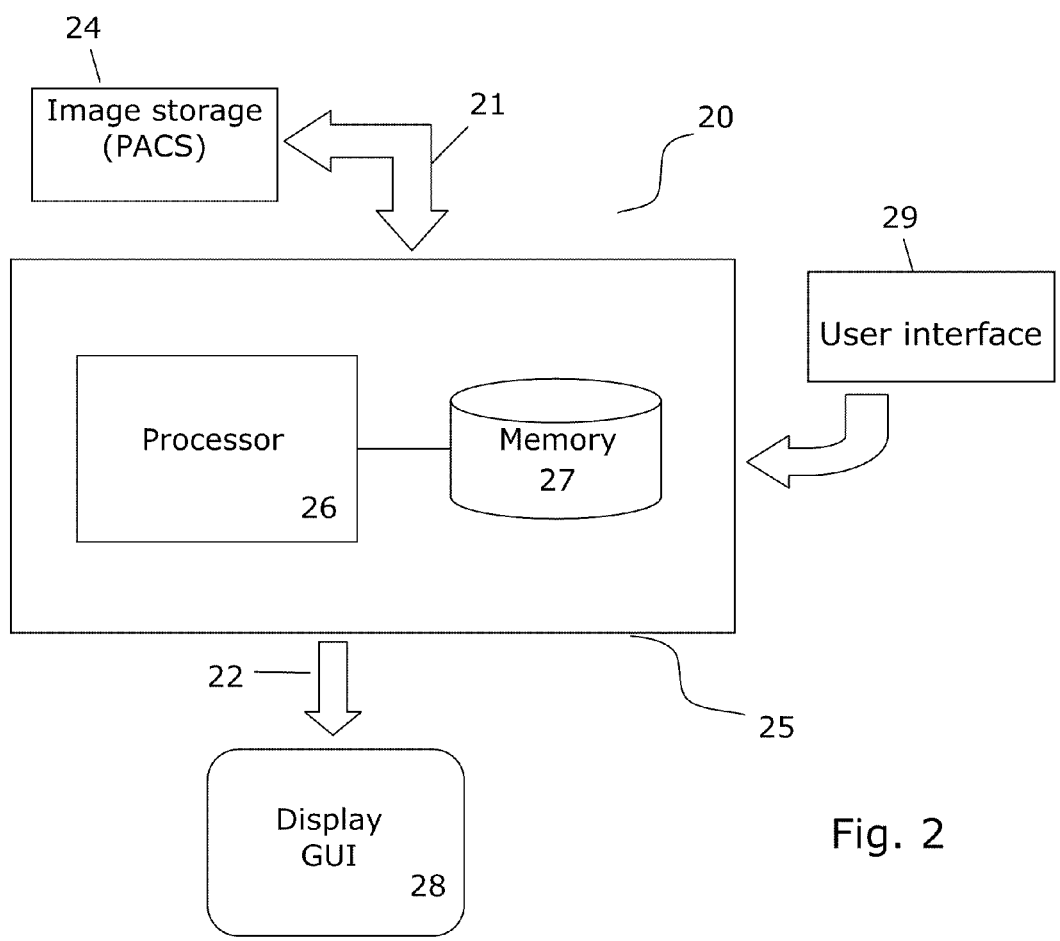
FIG. 2 illustrates a medical image analysis system 20 for implementing different embodiments for the various aspects of the invention.

FIG. 2 illustrates a medical image analysis system 20 for implementing different embodiments for the various aspects of the invention.

The system 20 has means 21 for receiving or accessing image data to be processed or already processed (i.e. post-processed) image data from an image recording apparatus such as a CT or MR scanner and/or internal or external storage 24 holding images recorded by such apparatus such as a PACS. The means 21 may e.g. be a data bus allowing access to a memory, an internet connection, or a cable or wireless connection. The system comprises a computer 25 or a similar processing apparatus holding an electronic processor 26 and memory 27 for holding and executing software or computer programs relating to the image analysis modules according to embodiments of the invention using the received image data. The system can further comprise user interface 29 (e.g. keyboard, mouse, touch screen etc.) for receiving user input. The determined corrections factors or corrected data or parameters can be presented to the user via a display 28 and/or stored in the storage 24.

As suggested, the storage may include access to a Picture Archival and Communication System (PACS). This is a system for storage of images and transferring images between computers in different facilities through networks. This system consists of devices to produce and store digital images electronically, workstations to view and interpret images, and a network linking computers from different sites. Appropriate PACS software allows the interpreter to manipulate images as needed, at his own location, by retrieving images from other locations via PACS. The PACS connects different computers through a high-speed network to share information. This connection can be in a single department using a local area network (LAN), in a hospital using the intranet, or outside the hospital via the Internet.

The individual elements of an embodiment of the invention may be physically, functionally and logically implemented in any suitable way such as in a single unit, in a plurality of units or as part of separate functional units. The invention may be implemented in a single unit, or be both physically and functionally distributed between different units and processors.

Correction for Extravascular Leakage

The estimating of contrast agent extravasation in contrast agent based perfusion imaging is described in the following with reference to the flow diagram 10 of FIG. 1.

INV: I have incorporated your new box, forgot tracked changes . . . . Dynamic perfusion imaging data reflecting MR signal intensity variations S(t) due to contrast agent administration is accessed (box 1), and pixel-wise converted to contrast agent concentration in tissue, C(t), as a function of time in voxels during the first and consecutive passages of the contrast agent through the vascular system, box 2.

In box 3, an estimated contrast agent concentration in plasma, $C_p'(t)$, such as preferably an AIF is determined, preferably automatically e.g. using the clustering method suggested in Bjornerud et al. However, other estimations of the contrast agent concentration may also be used. The signal is then represented by a convolution, $R_{ps}'(t) \otimes C_p'(t)$, of an apparent residue function, $R_{ps}'(t)$, and the (perfusion scaled) apparent residue function $R_{ps}'(t)$ can be determined by deconvolution of the signal with the estimated $C_p'(t)$, box 4.

In box 5, a first leakage rate constant $K_a$ quantifying an apparent rate of contrast agent extravasation from plasma to extravascular, extracellular space (EES) can be estimated based on a tail part of the apparent residue function $R_{ps}'(t)$ (or R'(t)).

Depending of the approach, it might be required to determine where, i.e. at which time, the tail part starts. For this purpose, the tail part of the apparent residue function can be determined in many different ways, such as by one or more of:

fitting a singly peaked, monotonously decreasing function, L(t), with zero asymptotes to a global maxima peak of the apparent residue function and defining the tail part of the apparent residue function as the part where the amplitude of the apparent residue function is consistently larger than the amplitude of L(t);

estimating the approximate mean transit time from the perfusion image data and from this estimate a time, $t_{tp}$, larger than MTT and using $R_{ps}'(t)$ for $t > t_{tp}$ as the tail part of the apparent residue function;

finding the section of the apparent residue function following its peak amplitude with minimum relative variance (variance divided by mean value) over a predefined section length; e.g. equal to a given fraction of the total number of data points from the peak to the last data point of the apparent residue function.

Fitting the apparent residue function to a composite of multiple functions describing the different portions of the residue function.

However, in other approaches involving fitting of functions to the apparent residue function, it may not be necessary to separately identify the tail part as the shape of the fitted function and the fitting procedure automatically extracts $K_a$ from the right part of $R_{ps}'(t)$.

Some preferred approaches for estimating $K_a$ is given here:
$K_a$ is estimated as being proportional to a mean value of the tail part of the apparent residue function.
$K_a$ is estimated as being proportional to an asymptote of the apparent residue function.
the estimation comprises fitting an exponential or linear function involving $K_a$ as a constant to at least the tail part of the apparent residue function.

It is noted that numerous other ways of determining Ka from the tail part of $R_{ps}'(t)$ can be made. Also, as extravasation is mainly an issue in pathologic tissue, it is generally not of specific interest to determine $R'(t)$, $K_a$, etc. for e.g. normal grey and white matter. It is therefore also possible to first perform a tissue segmentation and only make the determinations according to the invention in potentially pathologic tissue.

Optionally, as indicated in box 6, a second leakage rate constant $k_{ep}$ quantifying an apparent rate of contrast agent reflux from tissue back to blood (from EES back to IVS) can also be estimated based on the tail part of the apparent residue function. $K_a$ and $k_{ep}$ are preferably determined for each voxel in the image data.

When $K_a$ and optionally $k_{ep}$ have been determined, an extravasation corrected residue function, $R_{corr}(t)$, is preferably determined from the apparent residue function $R_{ps}'(t)$ and the estimated $K_a$, this is box 7.

The extravasation corrected residue function, $R_{corr}(t)$, is preferably determined using at least one of the following algorithms:

$$R_{corr}(t)=R'(t)-K_a$$

$$R_{corr}(t)=1/F(R_{ps}'(t)-K_a(1-k_{ep}t))$$

$$R_{corr}(t)=1/F(R_{ps}'(t)-K_a e^{-k_{ep}t})$$

$$R_{corr}(t)=1/F(R_{ps}'(t)-\text{mean}[R_{ps}'(t>t_{tp})])$$

where the residue function $R'(t)$ is scaled by a tissue flow, F, and wherein $t_{tp}$ is the estimated start time of the tail part as described above or a capillary transit time of the CA, $T_c$, described elsewhere.

Then (box 8), extravasation corrected hemodynamic parameters can be estimated using the first leakage rate constant $K_a$ or the extravasation corrected residue function $R_{corr}(t)$, preferably for each voxel. Typical parameters of interest are an extravasation-corrected CBV value, an extravasation-corrected mean transit time (MTT), and an extravasation-corrected bolus delay ($T_{max}$). An extravasation-corrected CBV value will reflect the true intravascular volume and is unaffected by contrast agent extravasation. In preferred embodiments, maps or images of the extravasation corrected hemodynamic parameters can be produced.

As mentioned previously, the sign of the tail part of the apparent residue function can be used to directly distinguish between $T_1$-dominant and $T_2^*$-dominant extravasation effects. Thereby, different maps or images can be generated for visualizing the dominant extravasation effect, based on a parameter related to the sign of the tail part of the apparent residue function, such as $\text{Sign}|R'(t \gg T_c)|$, $K_a$, $\text{Sign}|K_a|$, or similar.

Determined extravasation corrected values, functions, and parameters can be stored and/or presented to a user (box 9).

In more detail, a total contrast agent concentration in a voxel, $C_{t\_m}$, is related to the measured signal change induced by the contrast agent, which may be estimated as:

$$C_{t\_m}=C_{t\_ev}+C_{t\_iv},$$

wherein $C_{t\_iv}$ is the contrast agent concentration in tissue confined to the intravascular space in the absence of contrast agent extravasation as determined by a one-compartment model:

$$C_{t_{iv}}(t) = F\int_0^t R(t-\tau)C_p(\tau)d\tau.$$

And wherein $C_{t\_ev}$ is the contrast agent concentration in tissue confined to the extravascular space in the presence of contrast agent extravasation as determined by a two-compartment model:

$$C_{t_m}(t) = K_a\int_0^t e^{-k_{ep}(t-\tau)}C_p(\tau)d\tau + C_{t_{iv}}(t).$$

Thereby, $C_{t\_m}$ can be expressed as $$C_{t_m}(t) = \int_0^t [K_a e^{(-k_{ep}(t-\tau))} + F\cdot R(t-\tau)]C_p(\tau)d\tau$$

where $k_{ep}$ is the rate constant from the EES to the intravascular space, $C_p(\tau)$ is the contrast agent concentration in plasma, $R(t)$ is an effective tissue specific residue function, and F is proportional to tissue flow. $C_{t\_m}$ can be expressed in standard matrix notation as:

$$c=A(r+e)=A(r'),$$

where A is a convolution matrix for a contrast agent concentration in plasma, r is an effective tissue specific residue function, e is an error term due to constant agent extravasation involving $K_a$, and r' is the apparent' residue function and is given by:

$$r' = r+e = \begin{bmatrix} R(t_0) \\ R(t_1) \\ \vdots \\ R(t_{N-1}) \end{bmatrix} + \frac{K_a}{F}\begin{bmatrix} e^{-k_{ep}t_0} \\ e^{-k_{ep}t_1} \\ \vdots \\ e^{-k_{ep}t_{N-1}} \end{bmatrix}.$$

As mentioned above, r' can be determined by deconvolution of the signal by an estimated contrast agent concentration in plasma, preferably the arterial input function.

The present invention involves observing that the residue function contains an exponential "tail" in the presence of extravasation. The error term describing the error in CBV due to extravasation is then given by:

$$K_a\int e^{-k_{ep}t}dt.$$

Leakage rate constants $K_a$ and $k_{ep}$ can thereby be estimated directly from an apparent residue function obtained by deconvolution of the concentration signal, simply based on the tail of the apparent residue function. Several ways of performing this estimation is suggested herein.

In a preferred embodiment the non-leaky part of the apparent residue function (i.e. r or the peak corresponding to the duration of the first pass of contrast agent) can be approximated by a singly peaked function with zero asymptotes, e.g. a Lorenzian. Similarly, the error term (i.e. e or the tail corresponding to times following the first passage can be approximated by a function of $K_a$, e.g. a linear expression such as $K_a$ t or $K_a$ (1−$k_{ep}$t). Thereby, $K_a$ and optionally $k_{ep}$ can be determined by fitting these to the apparent residue function.

One approach to a more detailed derivation of the theory behind the present invention is provided in the following. This approach applies the assumption that the CA leaks into capillary tissue and EES simultaneously, which is a relatively good approach. Later in this description, another, alternative approach which instead assumes that CA extravasation occurs into first into capillary tissue and then, With a time lag, into EES will be presented. There are indications that this last approach better reflects the real situation, and although there is a large overlap in the two approaches, both are fully presented for completeness.

The approach to leakage correction applied by the present invention attempts to account for differences in MTT and delay and incorporate the correction directly into the convolution integral used to estimate tissue perfusion. In the absence of CA extravasation, tissue flow can be estimated by solving the convolution integral:

$$C_{t_{iv}}(t) = F \int_0^t R(t-\tau) C_p(\tau) d\tau \quad (1)$$

Where $C_p$ is the tracer concentration in plasma and $C_{t\_iv}$ is the tracer concentration in tissue (confined to the intravascular space), R is the tissue specific residue function and F is proportional to tissue flow. Given that $C_t$ and $C_p$ can be determined, perfusion (in units of mL/100 g/min) can then be estimated from the initial height of the residue function (in the absence of tracer delay) and is given by:

$$CBF = \frac{H_c}{\rho} F \quad (2)$$

where $H_c$ is a factor correcting for the difference in hematocrit in large vessels and capillaries and $\rho$ is tissue density. The mean transit time (MTT) is given by the area under the residue function and from the central volume principle blood volume (CBV) can then be estimated directly from the residue function according to:

$$CBV = CBF \cdot MTT = \frac{H_c}{\rho} F \int_0^t R(t) dt \quad (3)$$

In the situation where the tracer is not confined to the intravascular space, the tracer flux and reflux between the intravascular (i.v.) and extravascular-extracellular space (EES) can be described by a two compartment model as follows:

$$C_{t_m}(t) = K^{trans} \int_0^t e^{-k_{ep}(t-\tau)} C_p(\tau) d\tau + C_{t_{iv}}(t) \quad (4)$$

where $K^{trans}$ is the transfer constant from the i.v. space to the EES and $k_{ep}$ is the rate constant from the EES to the i.v. space, $C_p$ is the plasma concentration of tracer and $C_{t\_ev}$ is the tracer concentration in the extravascular space of tissue, $C_{t\_iv}$ is the intravascular tracer concentration.

Combining Eq. 1 and 4 and denoting $C_{t\_m}=C_{t\_ev}+C_{t\_iv}$ as the total tracer concentration in a voxel, we then obtain a single expression incorporating both CA dispersion and extravasation:

$$C_{t_m}(t) = \int_0^t [K^{trans e(-k_{ep}(t-\tau))} + F \cdot R(t-\tau)] C_p(\tau) d\tau \quad (5)$$

In DSC-MRI, relative CA concentration can only be estimated through measurements of change in the transverse relaxation rate ΔR2*. As discussed below, the apparent ΔR2* may be contaminated by T1-effects during CA extravasation and can therefore not be assumed to reflect CA concentration in the respective tissue compartments. Denoting the apparent rate constant estimated through measurements of ΔR2* in blood and tissue by K' and accounting for the discrete sampling interval Δt, Eq 5 can be written in matrix notation as:

$$\begin{bmatrix} \Delta R2'_t(t_0) \\ \Delta R2'_t(t_1) \\ \vdots \\ \Delta R2'_t(t_{N-1}) \end{bmatrix} = \Delta t \cdot \begin{bmatrix} \Delta R2'_p(t_0) & 0 & \cdots & 0 \\ \Delta R2'_p(t_1) & \Delta R2'_p(t_0) & \cdots & 0 \\ \vdots & \vdots & \ddots & \vdots \\ \Delta R2'_p(t_{N-1}) & \Delta R2'_p(t_{N-1}) & \cdots & \Delta R2'_p(t_{N-1}) \end{bmatrix} \times \left\{ F \cdot \begin{bmatrix} R(t_0) \\ R(t_1) \\ \vdots \\ R(t_{N-1}) \end{bmatrix} + K_a \cdot \begin{bmatrix} e^{-k_{ep}t_0} \\ e^{-k_{ep}t_1} \\ \vdots \\ e^{-k_{ep}t_{N-1}} \end{bmatrix} \right\} \quad (6)$$

In the case of contrast agent extravasations, we can thus substitute the 'non-leaky' residue function (r) with an 'apparent' residue function, r', given by:

$$r' = r + e = \begin{bmatrix} R(t_0) \\ R(t_1) \\ \vdots \\ R(t_{N-1}) \end{bmatrix} + \frac{K_a}{F} \begin{bmatrix} e^{-k_{ep}t_0} \\ e^{-k_{ep}t_1} \\ \vdots \\ e^{-k_{ep}t_{N-1}} \end{bmatrix} \quad (7)$$

Eq. 6 can then be written in simplified form as:

$$c = A(r+e) = Ar' \quad (8)$$

Now, for the situation where $k_{ep}t_{N-1} \ll 1$, the rate constant $K_a$ can be incorporated as the final element in the first residue term of Eq. 7 to give a single residue vector:

$$r' = \begin{bmatrix} R(t_0) \\ R(t_1) \\ \vdots \\ R(t_{N-1}) \\ K_a \end{bmatrix} \quad (9)$$

Equation 8 can then be solved for r' using standard deconvolution methods like singular value decomposition (SVD).

In a preferred embodiment, $K_a$ and optionally also $k_{ep}$ can be estimated directly from the apparent residue function r', i.e.

without the need for solving the equation system of Eq. 9. If $k_{ep}t_{N-1} \ll 1$, r' approaches a value of $K_a$ (rather than zero for no leakage). By ensuring that the total dynamic scan time is significantly longer than the tracer transit time in all tissues, $K_a$ can then simply be estimated from the offset value of r' for t>>MTT. If both $K_a$ and $k_{ep}$ are significant then the apparent residue function exhibits an exponential 'tail' given by $K_a \exp(-k_{ep}t)$ and the can then be estimated by fitting an exponential or a straight line to the tail of r'.

In another preferred embodiment, $k_{ep}t_N$ is assumed to negligible and $K_a$ can be estimated using either Eq 9 or by determining the mean offset level of the apparent residue function r'.

The determination of $K_a$ and optionally $k_{ep}$ from the apparent residue function is illustrated in the following referring to FIGS. 3A and B. Herein, the apparent residue function, R'(t), in the presence of $T_2^*$- or $T_1$-dominant extravasation (broken line curves in FIG. 3A or 3B, respectively) are shown relative to an ideal residue function, R(t), with no extravasation (solid line curve 30).

Figure 3A:
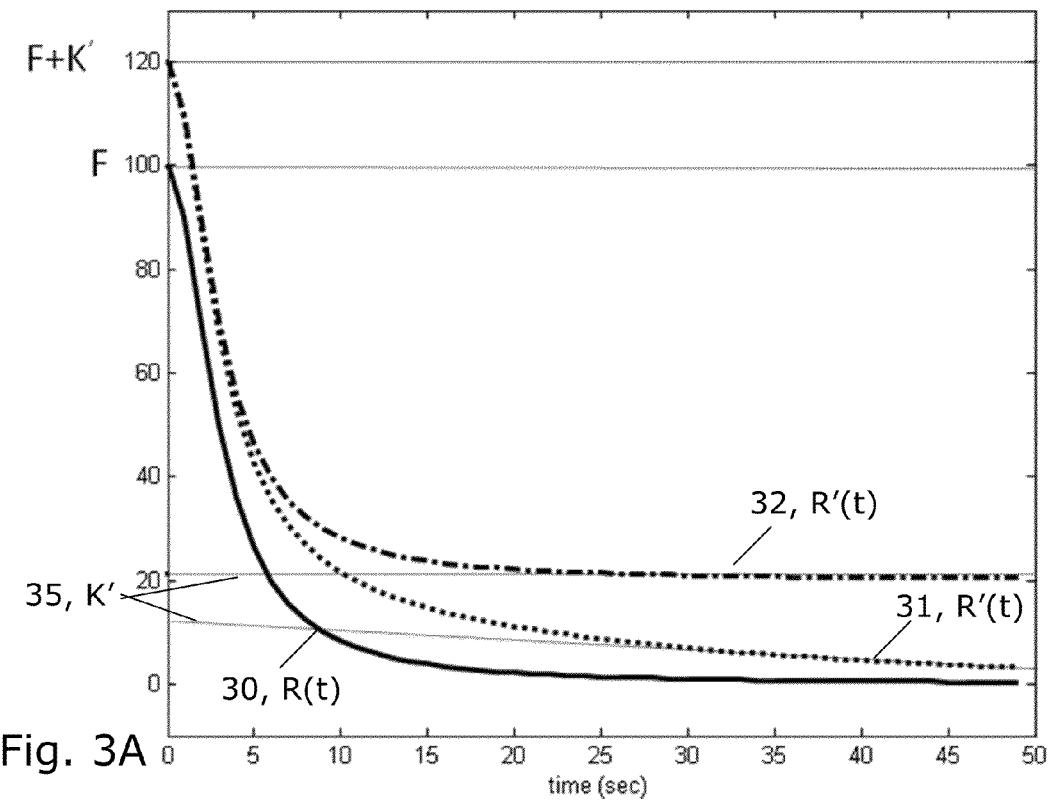
FIGS. 3A and B illustrate the determination of $K_a$ and optionally $k_{ep}$ from the apparent residue function R'(t).

FIG. 3A shows the apparent residue function in the presence of $T_2^*$-dominant extravasation. The dotted curve 31 represents the apparent residue function in the presence of both extravascular leakage ($K_a>0$) and backflux of contrast agent from tissue to blood ($k_{ep}>0$) whereas the dash-dot curve 32 represents the apparent residue function when $k_{ep}$ is negligible so that $k_{ep}t$ is approx zero for all time points. As seen, the apparent tissue perfusion is over-estimated by a factor $K_a$ in the presence of extravasation. In accordance with the invention, $K_a$ can be estimated (thin lines 35) from either the constant tail of the residue function (when $k_{ep}t \sim 0$, curve 32) or from the intercept of a linear fit of the tail of the apparent residue function when $k_{ep}t>0$, curve 31).

Figure 3B:
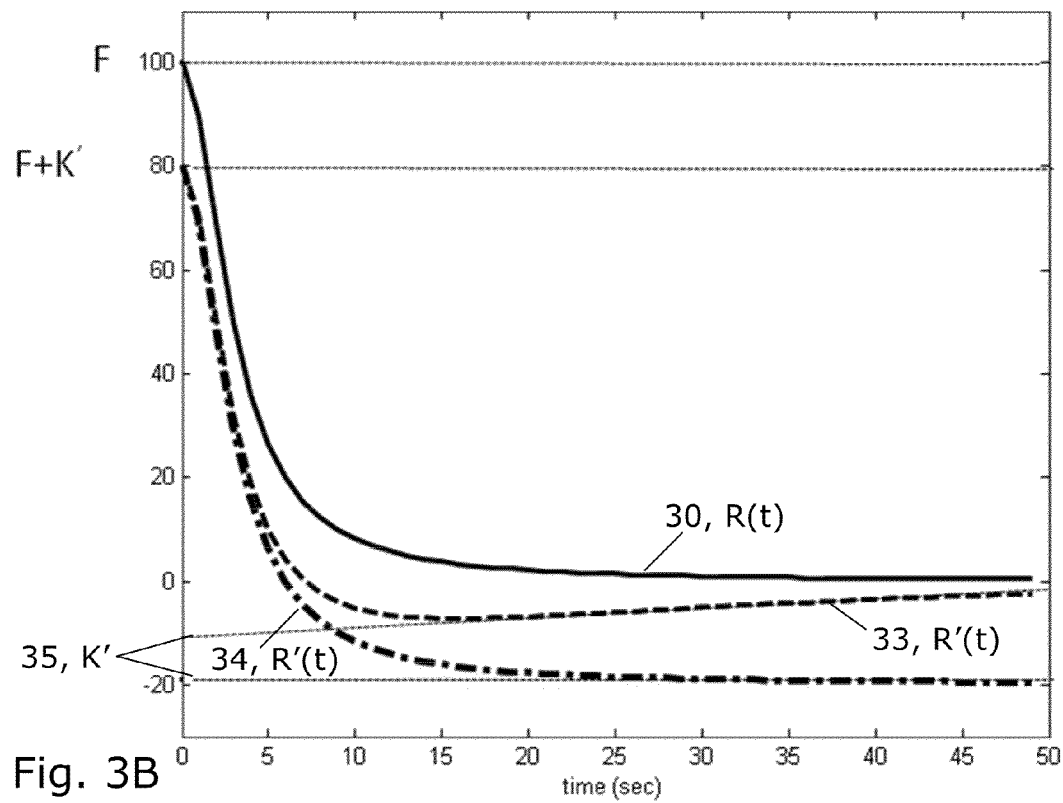

FIG. 3B shows the apparent residue function in the presence of $T_1$-dominant extravasation. The dashed curve 33 represents the apparent residue function in the presence of both extravascular leakage ($K_a<0$) and backflux of contrast agent from tissue to blood ($k_{ep}>0$) whereas the dash-dot curve 34 represents the apparent residue function when $k_{ep}$ is negligible so that $k_{ep}t$ is approximately zero for all time points. As seen, the apparent tissue perfusion is in this case under-estimated by a factor $K_a$ in the presence of extravasation. In accordance with the invention, $K_a$ can be estimated (thin lines 35) from either the constant tail of the residue function (when $k_{ep}t \sim 0$, curve 34) or from the intercept of a linear fit of the tail of the apparent residue function when $k_{ep}t>0$, curve 33).

When $K_a$ and optionally $k_{ep}$ have been determined, image data corrected to take into account extravasation of contrast agent can be calculated and stored and/or presented to a user. Alternatively or additionally, hemodynamic parameter can be calculated using the corrected image data and stored and/or presented to a user. In another alternative, a $K_a$ leakage map can be calculated and stored and/or presented to a user.

As an example, the leakage corrected CBV can be given by:

$$CBV_{corr} = CBV_{app} - K_a \Delta t N \quad (12),$$

where N is the number of data points in the AIF and $\Delta t$ is the sampling interval. The corrected flow value is similarly given by: $F' = F - K_a$. Note that $K_a$ is positive for T2* dominant leakage effects and negative for T1 dominant leakage, and as discussed below both T1 and T2* dominant leakage effects may be expected to occur in DSC-MR imaging of gliomas.

Figure 4:
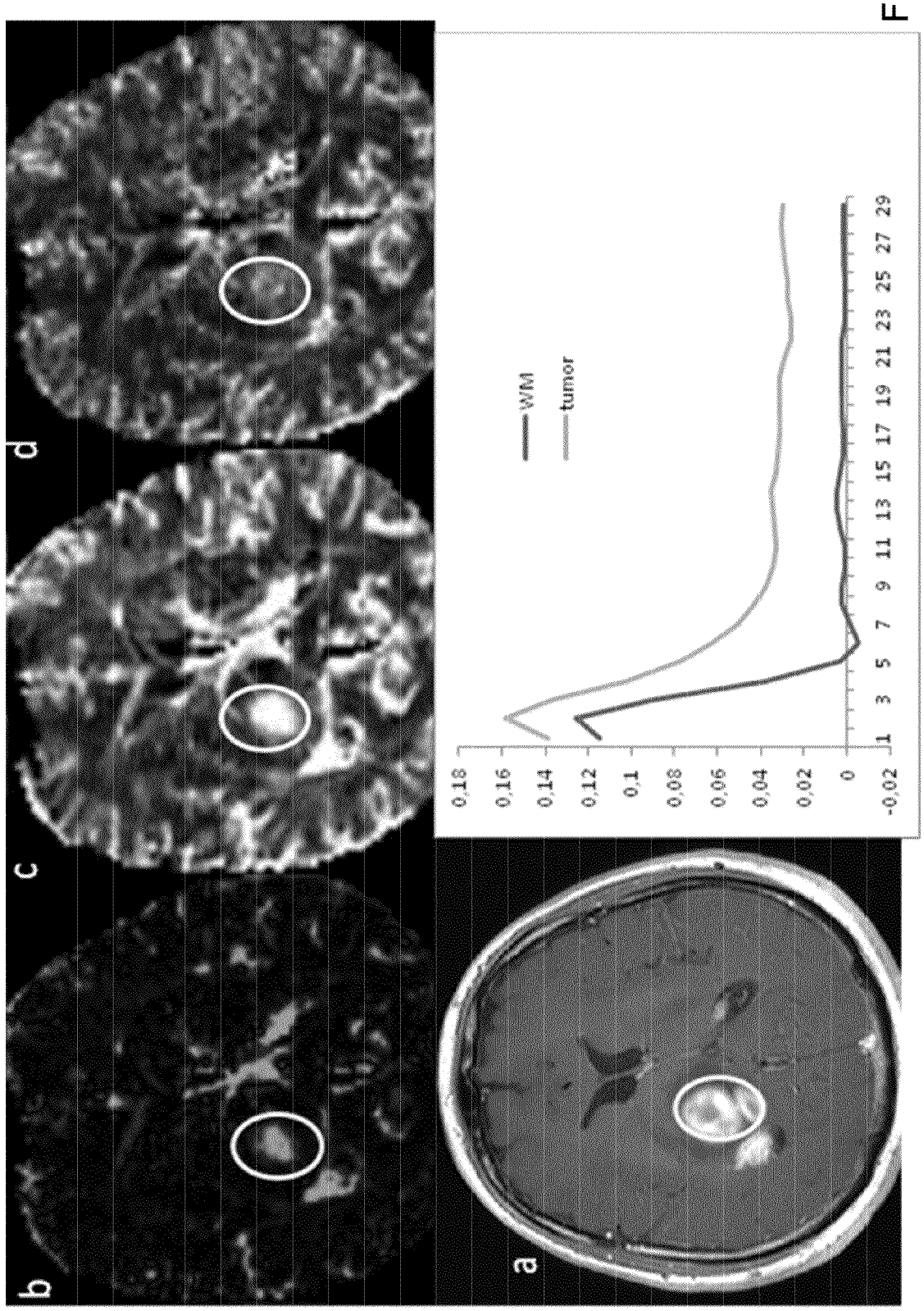
FIG. 4 shows a series of images from a clinical sample case of a grade 2 glioma with strong $T_2^*$ dominant leakage as well as a graph showing the corresponding apparent residue functions from normal white matter and tumor.

FIG. 4 shows a series of images from a clinical sample case of a grade 2 glioma with strong $T_2^*$ dominant leakage leading to an over estimation of CBV using prior art correction methods. The strong contrast agent leakage is apparent on the $T_1$-weighted post contrast image (image a). The resulting $K_a$ leakage map (image b) shows a region of $T_2^*$ dominant leakage in the tumor (white circle). The corresponding non-corrected CBV map (image c) shows region of significantly elevated CBV in the same region whereas the leakage corrected CBV map (image d) shows only slightly elevated CBV in the tumor region.

The lack of $T_2^*$-dominant leakage correction could in this case lead to a false positive diagnosis because the artificially high CBV values in the non-corrected image would be more suggestive of a high grade glioma. The corresponding apparent residue functions from normal white matter and tumor is shown in the graph of FIG. 4. The elevated tail of the apparent residue function from the tumor is clearly evident, and a value for $K_a$ may be estimated there from using the methods suggested herein.

PV Correction

Optimally, the contrast agent input should be a delta function where the contrast agent in the artery feeding the tissue of interest appears only at one point in time and then disappear. However, because it takes time to inject contrast material and the contrast material is injected in a peripheral vein, and because the body mixes contrast with blood, the actual contrast input function is more like an asymmetric bell curve and is customary estimated by the so-called the arterial input function (AIF). This means that the CTCs not only reflect the tissue perfusion, but also the input function of the contrast agent. In order to derive quantitative estimates of tissue perfusion, AIF is determined and a deconvolution of the CTC's with the AIF is performed.

But, the AIF is usually attenuated due to what is called partial volume effects. With an infinite resolution, reconstructed images should depict the contrast agent distribution uniformly and accurately throughout the field of view. However, because of the limited spatial resolution, "hot" spots (structures) relative to a "cold" background that are smaller than twice the resolution show partial loss of intensity, and the contrast agent concentration around the structure appears to be smeared over a larger area so that the structure appears to be larger and to have a lower activity concentration than it actually has. Similarly, a cold spot relative to a hot background would appear smaller with higher contrast agent concentration. Such underestimation and overestimation of concentration around smaller structures in the reconstructed images is called the partial-volume effect (PVE). As arteries (especially cerebral arteries) are typically smaller than the voxel size in the images, PVE's should be corrected for when making quantitative estimates of tissue perfusion.

A PV correction factor have traditionally been estimated from the ratio of the area under a venous CTC unaffected by PVE (since veins are generally larger in diameter) relative to the area under the CTC of the AIF. This method for PV correction is not very accurate when applied to MRI based images acquired with $T_2$- or $T_2^*$-weighted sequences. This is due to that the first-pass $T_2^*$-effect in voxels containing only blood is generally so large that complete signal loss occurs, with resulting venous CTC distortion.

Preferably, the automatic partial volume correction applied in an embodiment of the invention uses a novel approach where the pseudo steady-state (immediately following the first-pass phase) part of the respective CTCs of arteries and veins are used rather than the first-pass phase. The reason for doing this is that CTC inside veins are severely distorted by excessive T2* effects in DSC images and it is therefore very hard to determine correctly the area under the first pass curve from a vein. The steady-state effect is, however, not distorted to the same extent and by just measuring the difference in relative steady-state concentration in an artery and a vein we are able to determine the PV correction factor much more accurately. This approach is described in the following with reference to FIG. 1 in the following.

Perfusion image data comprising a signal related to contrast agent concentration as a function of time in voxels during the first and consecutive passages of the contrast agent through the vascular system is accessed or recorded and stored (box 1).

In box 2, AIF and a venous output function (VOF) are preferably be determined automatically. However, representation of contrast agent induced signal strength or other estimations of the contrast agent concentration may also be used.

In box 3, a PV correction factor, $f_{pv}$, is determined as a ratio between parts of the signals following the first passage of the contrast agent from one or more voxels comprising arterial blood and one or more voxels filled with venous blood, respectively.

When $f_{PV}$ has been determined, corrected image data wherein the signal is corrected to take into account PV effects can be calculated using $f_{PV}$ (box 4) and stored and/or presented to a user, box 6. Alternatively or additionally, hemodynamic parameters or a PVE-corrected arterial input function can be calculated using the image data and $f_{PV}$ (box 5) and stored and/or presented to a user, box 5.

The PV correction factor $f_{PV}$ can be determined per slice in the image data. Alternatively, $f_{PV}$ can be determined for the whole imaged volume, or for volumes of interest, such as a tumor region.

The following describes the theory of the PV correction according to an embodiment of the invention in more detail. According hereto, the pseudo-steady-state phase of the CTCs, i.e. the parts of the signals following the first passage of the contrast agent, can be used instead of the first-pass phase. This can be done under the assumption that the venous contrast agent concentration is here sufficiently low to avoid complete signal loss and signal distortion. Assuming that the dose-response is similar in arteries and veins in the steady-state phase and that the measured voxel-wise change in T2* relaxation rate is proportional to contrast agent concentration, the PV correction factor, $f_{pv}$, can be determined as:

$$C_{a\_ss}(t) = f_{pv} \cdot C_{v\_ss}(t) \quad (12)$$

where $C_{a\_ss}(t)$ and $C_{v\_ss}(t)$ are the steady-state concentrations in the identified arterial and venous voxels, respectively, e.g. the tails of AIF and VOF. It is assumed that the concentration levels in both the arteries and veins follow similar decay curves (or remained approximately constant) so that the mean concentration levels can be used and the PV correction factor can then be determined as the ratio of the mean steady-state concentrations:

$$f_{pv} = \frac{\text{mean}(C_{a\_ss})}{\text{mean}(C_{v\_ss})} \quad (13)$$

Having determined $f_{pv}$, an arterial input function corrected for PV effects can be determined:

$$C_a(t) = \frac{1}{f_{pv}} C_a^{PV}(t), \quad (14)$$

where $C_a^{PV}$ is the CA concentration in the AIF in the presence of PV effects. Hemodynamic parameters determined from the image data may be corrected in a similar fashion where necessary.

Arterial input functions (AIFs) and Venous output functions (VOFs) are preferably identified using the cluster analysis approach as described for the AIFs later herein, (but using a large CTC FM as the selection criterion for VOFs). Alternatively, one of the several known methods can be used to identify AIF and VOF.

Figure 5A:
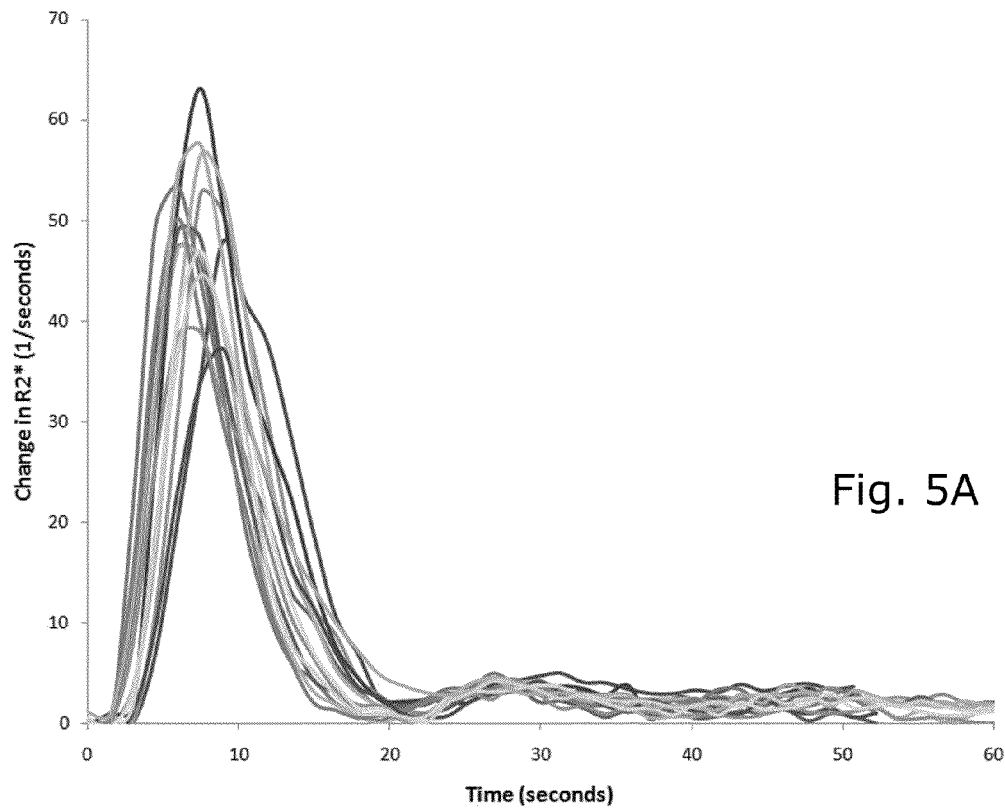
FIGS. 5A and B are graphs showing AIFs from multiple slice in a single subject corrected for PVEs.
Figure 5B:
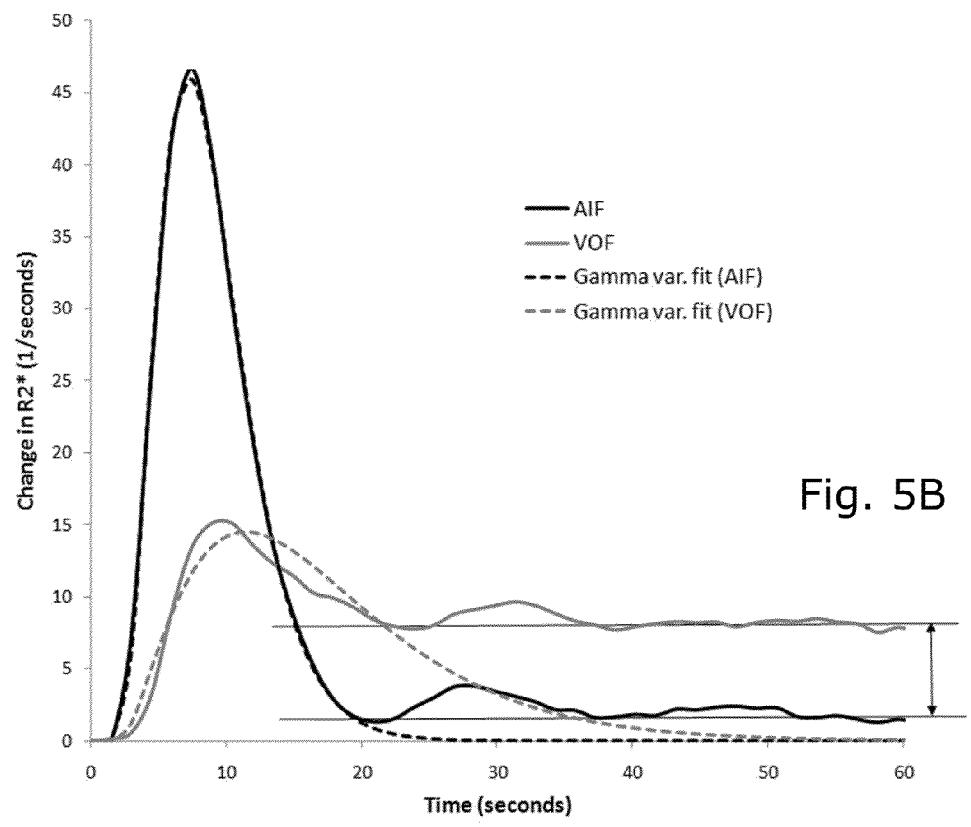

In one embodiment, the part of the signal following the first passage in the AIFs and VOFs can be estimated by first fitting a singly peaked function with zero asymptote, e.g. gamma-variate functions, to the respective CTCs. The CTC tails can be identified as the portion of the curves with amplitude above the corresponding value of the gamma-variate fitted curve (starting at the last time-point), as shown in FIG. 5B. A Fourier based low-pass filter can preferably be applied to the identified AIF and VOF prior to identification of the PV factor in order to improve the stability of the method. A number of specify alternative methods for determining the part of the signal following the first passage are specified in the claims.

When $f_{PV}$ has been determined, a PV corrected signal, or a function derived there from such as the AIF, can be determined and stored and/or presented using the determined PV correction factor, see e.g. Eq. 14 above. Alternatively or additionally, hemodynamic parameters corrected for PV effects can be calculated. As an example, blood volume values can be corrected as:

$$BV = f_{PV} BV^{PV},$$

where $BV^{PV}$ is the blood volume determined in the presence of PV effects.

In a demonstration of the methodology of the embodiment, AIFs from a number of subjects where corrected for PVEs. FIG. 5A shows AIFs automatically detected in each slice and FIG. 5B shows the corresponding average AIF across all slices together with the average venous output function (VOF), which was also based on VOFs determined individually in each slice (not shown). The corresponding gamma variate fitted curves are shown as dotted lines and the intersection points between the AIF/VOF and the gamma variate fitted curves were used to determine the steady-state portion of the respective curves as indicated. Finally the PV correction factor was determined from the difference in the steady state levels of the AIF and VOF, respectively as indicated by the arrow. A single PV correction factor was estimated for all slices based on the average steady-state concentration levels obtained from the identified arterial and venous CTCs. For each subject, the validity of the PV correction factor was assessed (from the criterion that $0 < f_{PV} \leq 1$) and any failure to detect at least one pixel representing a valid AIF in each slice was reported during the analysis.

The use of the PVE correction described above in an automated quantitative analysis of hemodynamic properties from contrast agent based perfusion imaging can be found in Bjørnerud and Emblem, A fully automated method for quantitative cerebral hemodynamic analysis using DSC-MRI, Journal of Cerebral Blood Flow & Metabolism (2010), 1-13.

CA Extravasation Correction Applied to Tumor Perfusion Imaging

The following describes estimation of contrast agent extravasation according to an embodiment of the invention and its application to tumor perfusion imaging using MRI. The method according to an embodiment of the invention is also compared to prior art methods for comparison. The correction method described herein is based on the approach where it is assumed that CA extravasation occurs into first into capillary tissue and then into EES. This is an alternative to the approach assuming simultaneous extravasation described previously in the section "Correction for extravascular leakage".

The following describes an embodiment of the CA extravasation correction method according to the various aspects of the invention. The method enables semi-quantitative determination of the transfer constant and can be used to distinguish between $T_1$- and $T_2^*$-dominant extravasation effects while being insensitive to variations in tissue mean transit time (MTT). Results in 101 patients with confirmed glioma suggest that leakage-corrected absolute cerebral blood volume (CBV) values obtained with the proposed method provide improved overall survival prediction compared to normalized CBV values combined with an established leakage correction method. Using a standard gradient-echo echo-planar-imaging sequence, about 60% and 10% of the tumors with detectable contrast agent extravasation exhibited mainly $T_1$- and $T_2^*$-dominant leakage effects, respectively. The remaining 30% of leaky tumors had mixed $T_1$- and $T_2^*$-dominant effects. Using a MTT-sensitive correction method, our results show that CBV is underestimated when the tumor MTT is significantly longer than MTT in reference tissue.

Contrast agent (CA) extravasation is a general problem for all DSC-based MRI methods used for brain tumor assessment since the kinetic models used explicitly assume that the CA remains in the intra-vascular space for the duration of the dynamic acquisition. Studies suggest that CA leakage can lead to either over- or under-estimation of relative CBV (rCBV) in tumors with blood-brain-barrier breakdown unless specifically corrected for. A correction method where CA extravasation is estimated in each voxel by determining the voxel-wise deviation from a 'non-leaky' reference tissue response curve has been proposed. This approach is appealing in that it does not require the use of non-standard imaging sequences or CA injection schemes and the method has been shown to improve the diagnostic accuracy of DSC-MRI in glioma grading (Boxerman et al. 2006). The potential limitation of the method is that the model assumes that MTT and bolus arrival time is the same in tumor and non-pathological tissue. Quarles et al (Quarles et al. 2005) showed, based on simulations and data in a rat gliosarcoma model that this leakage correction method may result in incorrect rCBV values in tumors with significant alteration in the hemodynamic state. Based on this observation they proposed an alternative method where CA extravasation is accounted for by incorporating a leakage term in the tissue residue function, thereby providing an MTT-insensitive estimate of the transfer constant describing the CA flux between the intra-vascular- and extra-vascular extra-cellular space (IVS and EES).

The present invention proposes an alternative approach where the transfer constant is determined directly from the tissue residue function. From this, a direct estimation of perfusion metrics and MTT-insensitive CA extravasation from the resulting tissue residue function can be derived. In a preferred aspect, this may be combined with a fully automated approach for quantitative DSC-MRI incorporating automatic slice-wise detection of the AIF and partial volume (PV) correction.

Theory
Estimation of Tumor Hemodynamic Parameters in the Presence of CA Extravasation A correction method is described by Boxerman et al (Boxerman et al. 2006) where CA extravasation is estimated in each voxel by determining the voxel-wise deviation from a 'non-leaky' reference tissue response curve:

$$\Delta R2^*(t) \approx K_1 \cdot \overline{\Delta R2^*(t)} - K_2 \int_0^t \overline{\Delta R2^*(t')} dt' \quad (15)$$

where $\Delta R2^*(t)$ is the measured CA induced change in transverse relaxation rate ($1/T_2^*$) in the presence of CA extravasation, $\overline{\Delta R2^*(t)}$ is the average $\Delta R2^*(t)$ in voxels with no CA extravasation, $K_1$ and $K_2$ are scaling constants for relative blood volume and permeability, respectively. The negative sign of $K_2$ is due to the assumed $T_1$-dominant CA relaxation effect in the EES. Relative CBV is given by the area under the first-pass response, and it thus follows that the leakage corrected rCBV is given by:

$$rCBV_{corr} = rCBV + K_2 \int_0^T dt'' \int_0^{t''} \overline{\Delta R2^*(t')} dt' \quad (16)$$

This approach will be used as the reference correction method in the current work. One potential limitation of this method is that it explicitly assumes that MTT in a leaky voxel is identical to the MTT of the mean tissue response curve (Quarles et al. 2005). This can be seen from Equation 15 because, in the absence of extravasation, any given response curve should be related to the reference curve by a single scaling constant ($K_1$). Any deviations in MTT (or CA delay) would thus introduce an incorrect non-zero value of $K_2$.

An alternative approach accounting for variations in tissue MIT is to estimate CA extravasation from the tissue residue function obtained following AIF deconvolution. In the absence of CA extravasation, tissue flow can be estimated from the convolution integral:

$$C_{t\_iv}(t) = f \int_0^t R(t) C_p(t - \tau) d\tau \quad (17)$$

where $C_p$ is the tracer concentration in plasma and $C_{t\_iv}$ is the tracer concentration in tissue (confined to the IVS), $R(t)$ is the tissue specific residue function and f is tissue flow (in units of 1/s). Given that CA concentration in blood and tissue can be determined, f and $R(t)$ can be estimated by deconvolution, and perfusion (in units of mL blood/100 g/min) is then given by:

$$CBF = \frac{H_c}{\rho} f \quad (18)$$

where $\rho$ is tissue density and $H_c=1-Hct_{art}/1-Hct_{cap}$ takes into account differences in hematocrit values in large vessels and capillaries. The MIT is given by the area under the residue function and, in the absence of CA extravasation, CBV can then be estimated from the central volume principle:

$$CBV = CBF \cdot MTT = \frac{H_c}{\rho} f \int_0^\infty R(t) dt \quad (19)$$

If the tracer is not confined to the IVS, CA extravasation can be expressed in terms of a two compartment model:

$$C_{t\_ev}(t) = K^{trans} \int_0^t \exp(-K^{trans}(t - \tau)/v_e) \cdot C_p(t) d\tau \quad (20)$$

where $K^{trans}$ is the transfer constant describing the CA flux from the IVS to the EES, $v_e$ is the leakage space per unit volume and $C_{t\_ev}$ is tracer concentration in the EES. It is noted, that the reflux rate constant $k_{ep}$ previously used to quantify a rate of contrast agent reflux from EES to IVS elsewhere (under the assumption that CA leaks into capillary tissue and EES simultaneously). From conservation of mass, the constant $k_{ep}$ is related to $K^{trans}$ by the expression: $k_{ep}=K^{trans}/V_e$ where $V_e$ is the fractional distribution volume of the contrast agent in the EES. For clarity and compliance with literature, $k_{ep}$ will be replace by $K^{trans}/V_e$ in the following.

In order to estimate both perfusion and permeability from a single acquisition, a combined model of the two processes is needed. We base our combined analysis approach on the adiabatic approximation to the tissue homogeneity model. Here, the intra-vascular response is modelled as a function of both time and distance along the capillaries and it is assumed that the dynamic time course is separable into an early (fast) vascular phase followed by a (slow) extravasation phase. The tissue response, including both the intra-vascular- and extra-vascular responses can then be expressed as:

$$C_{t\_m}(t) = f\int_0^t R(t)C_p(t-\tau)d\tau + K^{trans}\int_{T_c}^{t'} \exp(-K^{trans}(\tau-T_c)/v_e)\cdot C_p(t'-\tau)d\tau \quad (21)$$

where $T_c$ is the capillary transit time of the CA so that $t<T_c$ and $t'\geq T_c$. The combined residue function H(t) scaled by flow and the extravasation transfer constant can then be expressed as:

$$H(t)\approx f\cdot R(t) \quad 0\leq t<T_c$$

$$H(t)\approx K^{trans}\cdot\exp(-K^{trans}(t-T_c)/v_e) \quad t\geq T_c \quad (22)$$

Complete separation of the intra-vascular- and extravasation phase using this model requires R(t) to be a box function so that R(t)=1 for $0\leq t<T_c$ and R(t)=0 for $t\geq T_c$. However, since the intra-vascular residue function is in reality a monotonically decreasing probability function the two phases will overlap and $T_c$ is an average transit time (MTT) for all capillary paths. However, for $t\gg T_c$, H(t) is dominated by the leakage term and by further assuming limited reflux within the measurement time, $T_N$, so that $K^{trans}T_N/v_e\ll 1$, we get:

$$H(t)\approx K^{trans} \quad t\gg T_c \quad (23)$$

Dose Response Considerations

In DSC-MRI, CA concentration can only be estimated in relative terms through measurements of change in transverse relaxation rate ($\Delta R2^*$ or $\Delta R2$) which in turn is estimated from measured change in MR signal intensity (SI). In single shot GRE-EPI sequences used in DSC-MRI, the SI can be approximated by the steady-state expression:

$$SI(C) = M_0\frac{\sin(\alpha)(1-\exp(-TR\cdot R1(C)))}{1-\cos(\alpha)\exp(-TR\cdot R1(C))}\exp(-TE\cdot R2^*(C)) = M_0 E1(C)\cdot\exp(-TE\cdot R2^*(C)) \quad (24)$$

where $M_0$ is proportional to the equilibrium magnetization, C is the CA concentration, R1, R2* are $T_1$- and $T_2^*$ relaxation rates, respectively, TE is the echo time and $\alpha$ is the flip angle. The change in SI due to CA induced increase in relaxation rates can then be expressed as:

$$\frac{1}{TE}\left[\ln\left(\frac{SI(0)}{SI(C)}\right)\right] = \Delta R2^*(C) - \frac{1}{TE}\ln\left(\frac{E1(C)}{E1(0)}\right) = \Delta R2^*_{app}(C) \quad (25)$$

where $\Delta R2^*$ is the change in $T_2^*$ relaxation rate, $\Delta R2^*_{app}$ is the measured apparent change in $\Delta R2^*$ including $T_1$-effects and E1(C)>E1(0). In DSC imaging, the $T_1$-term in Equation 25 is commonly assumed to be negligible compared to the much stronger $T_2^*$ relaxation effects for an intra-vascular CA distribution. In the case of CA extravasation $T_1$-relaxation effects may become significant due to a reduction in CA compartmentalization (reduced $T_2^*$-relaxation) combined with increased distribution volume and water access to the paramagnetic centre of the CA. Hence, the extravascular CA induced signal change is more difficult to predict, and both $T_1$- and $T_2^*$ effects may dominate when CA is present in the EES.

From this, it cannot be assumed that the transfer constant measured from a single echo DSC-MRI acquisition reflects the underlying $K^{trans}$. We therefore distinguish between the apparent transfer constant, $K_a$, estimated through measurements of $\Delta R2^*$ combined with the proposed models, and the true transfer constant $K^{trans}$ as defined in Equation 20. Using this notation, Equation 7 can be written in matrix notation in terms of the measured changes in $T_2^*$ relaxation rates as:

$$Y = A\cdot h \quad (Tb\ 26)$$

where $$Y = \begin{bmatrix} \Delta R2_t^*(t_0) \\ \Delta R2_t^*(t_1) \\ \vdots \\ \Delta R2_t^*(t_{N-1}) \end{bmatrix} \quad (27)$$

$$A = \Delta t\cdot\begin{bmatrix} \Delta R2_a^*(t_0) & 0 & 0 & 0 \\ \Delta R2_a^*(t_1) & \Delta R2_a^*(t_0) & \ldots & 0 \\ \vdots & \vdots & & \vdots \\ \Delta R2_a^*(t_{N-1}) & \Delta R2_a^*(t_{N-2}) & \ldots & \Delta R2_a^*(t_0) \end{bmatrix} \quad (28)$$

and $$h = r + e = f\begin{bmatrix} R(t_0) \\ R(t_1) \\ \vdots \\ R(t_C) \\ 0 \\ 0 \\ \vdots \\ 0 \end{bmatrix} + K_a\begin{bmatrix} 0 \\ 0 \\ \vdots \\ 0 \\ 1 \\ \exp(-K^{trans}\Delta t/v_e) \\ \vdots \\ \exp(-K^{trans}(N-1)\Delta t/v_e) \end{bmatrix} = \begin{bmatrix} H(t_0) \\ H(t_1) \\ \vdots \\ H(t_{N-1}) \end{bmatrix} \quad (29)$$

where $\Delta t$ is the sampling interval, N is the number of datapoints, $t_c$ is the time index corresponding to $T_c$, $\Delta R2_t^*$ is the apparent change in R2* in tissue in the presence of $T_1$-effects and extravasation (Equation 25) and $\Delta R2_a^*$ is the corresponding change in R2* in blood. Equation 26 can be solved for h using standard matrix inversion methods like singular value decomposition (SVD) and $K_a$ is then approximated from the tail of H(t) following the assumptions leading up to Equation 23.

The apparent blood volume measured in a leaky voxel is given by the area under H(t), which can be expressed in terms of the intra-vascular ($v_i$) and extra-cellular ($v_e$) volume fractions as follows:

$$v_T \approx f\int_0^{T_c} R(t)dt + K_a\int_{T_c}^\infty \exp(-K^{trans}(t-T_c)/v_e)dt = v_i + v_e \quad (30)$$

The intra-vascular blood volume (in units of mL blood/100 g) is then given by:

$$CBV_i = \frac{H_c}{\rho}(v_T - v_e) \quad (31)$$

Since we have assumed negligible CA reflux within the total sampling time, $v_e$ cannot be estimated but the error in $CBV_i$ due to CA extravasation can then be estimated from the approximation $H(t) \approx K_a$ for $t \gg T_c$ so that the leakage corrected intra-vascular blood volume is given by:

$$CBV_{corr} = CBV_{app} - K_a \Delta t (N - N_c)/\rho; N \Delta t K^{trans}/v_e \ll 1 \quad (32)$$

where $CBV_{app}$ is the apparent CBV value measured by Equation 19 and $N_c$ is the time index corresponding to $T_c$. $T_c$ is unknown and tissue dependent but may be estimated by fitting the initial portion of H(t) to an appropriate parametric function. CBF is not affected by CA extravasation effects since $H(t)=fR(t)$ ($t \ll T_c$) is not dependent on $K_a$.

Methods
Patient Material

Study approval was obtained from the Regional Medical Ethics Committee and patients were included only if informed consent was signed. A total of 101 patients (51 males, mean age 51 years, range 8-79 years) with confirmed glioma, selected from an ongoing prospective tumor perfusion study were included in the analysis. The histopathological diagnosis of the included patients is specified in a previous study (Bjornerud and Emblem 2010), and for the current work the patients were divided into two groups where glioma grades I and II were grouped as low grade gliomas (LGG) and glioma grades III and IV were grouped as high grade (HGG).

MR Imaging

Imaging was performed at 1.5 Tesla (Siemens Sonata, Symphony or Avanto, Siemens AG, Erlangen, Germany), using an 8-channel-(Symphony/Sonata) or a 12-channel (Avanto) head-coil. DSC MRI was performed using a GRE-EPI sequence acquired during CA administration. The DSC imaging parameters were: TR/TE/flip angle 1430 ms/46 ms/90°, bandwidth 1345 Hz/pixel (12 axial slices) or 1720/48, bandwidth 1500 Hz/pixel (14 axial slices), field of view 230×230 mm², voxel size 1.8×1.8×5 mm³, inter-slice gap 1.5 mm. For each slice, 70 images were recorded at intervals equal to the repetition time (TR). After eight time-points, 0.2 mmol/kg of the CA gadobutrol (Gadovist™, Bayer Schering Pharma AG, Berlin, Germany) was injected at a rate of 5 mL/s, immediately followed by a 20 mL bolus of saline (B. Braun Melsungen AG, Melsungen, Germany), also at 5 mL/s. The image protocol included axial $T_2$-weighted fast spin-echo (FSE) images (TR/TE=4000 ms/104 ms), coronal fluid attenuated inversion recovery (FLAIR) images (TR/TE=9050 ms/114 ms and TI=1500 ms) and axial $T_1$-weighted SE images (TR/TE=500 ms/7.7 ms) obtained before and after i.v. CA injection. The voxel size was 0.45×0.45×5 mm³ with 19 slices for the $T_2$- and $T_1$-weighted images and 0.9×0.9×5 mm³ with 25 slices for the FLAIR images.

Data Analysis
Perfusion Analysis and Extravasation Correction

The proposed extravasation correction methods was compared to the reference method of Boxerman et al (Boxerman et al. 2006, or U.S. Pat. No. 6,807,441), referred to as Method I. Different from the original implementation, the constant $K_2$ (Equation 15) was allowed to assume both positive and negative values in order to account for the possible presence of both $T_1$- and $T_2^*$-dominant relaxation effects during CA extravasation. In the proposed alternative method (denoted Method II) the apparent transfer constant $K_a$ was determined directly from the tail of the residue function as outlined in the Theory section. Method I was used only to correct relative CBV values normalized to unaffected white matter whereas Method II provided absolute estimates of CBF and leakage corrected CBV and MTT from the residue function. The residue function was determined on a pixel-by-pixel basis (or from simulated response-curves) using iterative Tikhonov-regularized SVD (iTrSVD) deconvolution. The intravascular residue function R(t) was estimated by fitting the initial portion (first five time points) of H(t) to a Lorentzian function of the form:

$$R(t) = \left[1 + \left(\frac{\pi \cdot t}{2T_c}\right)^2\right]^{-1} \quad (33)$$

where $T_c$ is the intravascular transit time which was then used as an estimate of the cut-off point between the intravascular phase and the extravasation phase corresponding to the tail part (Equation 22). The curve fit was performed using a Levenberg-Marquardt non-linear least squares fitting procedure. The Lorentzian function provided excellent goodness of fit to actual residue functions obtained in unaffected white and grey matter (data not shown).

Simulations

Simulations were performed to investigate the validity of the two extravasation correction methods under different hemodynamic conditions and to assess the sensitivity of the models to variations in underlying tissue relaxation properties and sequence parameters. For all simulations the AIF was modelled as a gamma-variate function, but with an additional exponential term to model steady-state effects:

$$Ca(t) = \quad (34)$$
$$(t-T_0)^a \exp\left(-\frac{t-T_0}{b}\right) + Ca_{ss}\left(1 - \exp\left(-\frac{t-T_{0ss}}{\beta}\right)\right)\exp\left(-\frac{t-T_{0ss}}{T_{el}}\right)$$

where a, b β are curve shape constants, $T_0$ is the CA arrival time, $T_{0ss}$ is a time delay constant for the steady-state effect, $Ca_{ss}$ is the steady-state CA concentration and $T_{el}$ is the plasma elimination half-life of the CA. The constants were chosen such that $Ca_{max}=7$ mM and $Ca_{ss}=1$ mM. A Lorentzian intravascular residue function (Equation 33) was used for all simulations.

Dependence of $K_a$ on Transverse Relaxivity and Sequence Parameters

The concentration time curves $C_{t\_iv}(t)$ and $C_{t\_ev}(t)$ were estimated from the AIF by convolution (Equations 17 and 20) for given values of MTT, CBF, $K^{trans}$ and $v_e$ and the corresponding relaxation rates changes in the respective compartments were calculated as described below. Signal changes corresponding to the estimated CA induced relaxation rate changes were then calculated using the expression for steady-state GRE signal behaviour (Equation 25) and the corresponding changes in apparent R2* relaxation rates were cal culated from the simulated signal changes, assuming negligible $T_1$-effects:

$$\Delta R2^*_{app}(C) = \frac{1}{TE} \ln\left(\frac{SI(0)}{SI(C)}\right) \quad (35)$$

$R2^*_{app}$ in tissue was then deconvolved with the AIF R2* response curve in order to estimate the residue function measured in the presence of extravasation and tissue relaxation effects. Finally, $K_a$ was extracted from the residue function using Method II as described in the Theory section.

The tissue $T_1$- and $T_2^*$-relaxation rates were estimated by assuming linear dose-response functions:

$$R2^*(C) = R2^*(0) + r2 \cdot C$$

$$R1(C) = R1(0) + r1 \cdot C \quad (36)$$

where r1 and r2 are the $T_1$- and $T_2^*$-CA relaxivities, respectively in a given tissue compartment and R1(0) and R2*(0) are the relaxation rates in the absence of CA. Change in tissue $T_1$-relaxation was assumed to be a function of extra-vascular CA concentration only, assuming the intra-vascular $T_1$-relaxation contribution in tissue to be negligible. The CA-induced change in R2* relaxation rates were assumed to be a linear combination of the intra-vascular and extra-vascular contributions:

$$\Delta R2_t^*(C_{ev},C_{iv}) = \Delta R2_{ev}^*(C_{ev}) + \Delta R2_{iv}^*(|C_{iv}-C_{ev}|) \quad (37)$$

The dependence of $\Delta R2^*_{iv}$ on $\Delta C = |C_{iv}-C_{ev}|$ is due to the fact that $\Delta R2^*_{iv}$ is proportional to the susceptibility difference ($\Delta X$) between the two compartments and $\Delta \chi \propto \Delta C$. The effect of variations in extra-vascular structure and volume was simulated by varying the effective transverse relaxivity, $r2_{ev}$ in the EES. The value of $r2_{ev}$, was initially set equal to the dipolar value as obtained in a completely homogeneous solution (r2=5.3 mM$^{-1}$s$^{-1}$). This was assumed to be the lower limit in tissue with complete loss of cellular integrity. In tissue with intact cell membranes, $r2_{ev}$ will be higher due to field perturbations at the intra- and extra-cellular interface. The effect of increasing degree of compartmentalization was simulated by a step-wise increasing of $r2_{ev}$ up to a maximum value of 30 mM$^{-1}$s$^{-1}$. For the intra-vascular contribution, $r2_{iv}$=44 mM$^{-1}$s$^{-1}$ was used, a value which was previously found to be valid for both grey and white matter in the brain at 1.5 T.

A linear dose-response was also assumed for the AIF. Although studies have shown that R2* relaxation in large arteries is quadratically dependent on the CA concentration, the automated AIF determination implemented in the current work tends to select voxels located outside the large arteries where a linear R2* dose response and absence of $T_1$ relaxation effects can be assumed. The tissue contribution to the AIF was assumed to be negligible and an arterial R2* relaxivity $r2_a$ of 8 mM$^{-1}$s$^{-1}$ was used. The value of $r2_a$ was taken as being close to the linear component of the intra-vascular relaxivity previously described, a value which was also found to give AIF R2* response curves in good agreement with results in patient data. For $T_1$-relaxivity in the EES, r1=4.2 mM$^{-1}$s$^{-1}$ was used.

$K_a$ estimated from the above method was compared to the actual $K^{trans}$ over a relevant range of $K^{trans}$ (corresponding to extraction fractions $0 \leq E \leq 0.5$ where $E = K^{trans}/f$). Sequence parameters were kept constant except for the flip angle that was varied between 30° and 90°. The effect of using a pre-dose was also simulated by estimation of the respective CA concentrations in all compartments following a first injection, and using these concentration values as baseline values for a second injection. The following additional parameters were fixed for all simulations: TR/TE=1500 ms/45 ms, CBF=80 mL/100 g/min and MTT=5 s.

MTT Dependence

Using pre-defined values of CBF, MTT and $K_a$ tissue response curves were generated according to Equations 27-29. Gaussian noise corresponding to an SNR of 50 in the raw data was added. Defining the apparent extraction fraction as $E_a = K_a/f$, simulations were performed with $E_a = 0.1$ and $E_a - 0.1$ to model both $T_1$-($E_a$<0) and $T_2^*$-($E_a$>0) dominant extravasation effects. The simulated leakage affected response curves were then used to estimate $K_a$ or $K_2$ and the corresponding leakage corrected perfusion metrics obtained using the two correction methods where compared to the same values in the absence of extravasation. When applying correction Method I to the simulated data, a reference tissue response curve with $E_a = 0$, MTT=5 s and CBF=40 mL/100 g/min was assumed and a leakage corrected response curve was generated from Equation 15. When varying MTT, CBF was kept constant at 80 mL/100 g/min so that CBV varied as a function of MTT. Finally, in the case of no extravasation, MTT varied between 0.5 and 4 times the corresponding MTT in reference tissue (0.5<nMTT<4). For a given nMTT, the error in $K_2$ (i.e. deviation from zero) and corresponding error in the leakage corrected rCBV value was estimated. The error in rCBV was estimated as the percent difference between rCBV values obtained when applying leakage correction according to Method I compared to the values obtained without applying leakage correction.

All data simulations were performed in Matlab 2007a (MathWorks, Natick, Mass.)

Comparison of Extravasation Correction Methods in Patient Data

The sensitivity of correction Method I to variations in MTT was tested based on pixel-wise analysis in selected tumors (with tumor MTT values deviating from MTT in non-pathological tissue) and compared to the expected results based on the simulations. Leakage corrected MTT values (obtained using correction Method II) were extracted from each voxel within the tumor region-of-interest (ROI) and normalized to the MTT derived from a mask of unaffected white and grey matter to yield nMTT values which were correlated to the corresponding pixel-wise $K_2$ and $K_a$ values. In order to estimate the error in $K_2$ as a function of nMTT, $K_a$ was assumed to be linearly related to $K_2$ for values of nMTT close to unity. Selecting only tumor pixels with nMTT≈1 the linear correlation coefficient was then estimated so that $K_2^{est} = \alpha K_a$. Under the assumption that $K_a$ is independent of nMTT the error in $K_2$ as a function of nMTT was then $\Delta K_2 = \alpha K_a - K_2$. The same tissue mask used to extract normalized MTT values was used to determine the reference tissue response curve when estimating $K_2$ according to Method I (Equation 15) so that for pixels with nMTT≈1 it would be expected that $1K_2 \approx 0$. Finally, under the assumption that corrected CBV obtained from Method II (CBV(II)) is independent of nMTT, the percent difference between CBV(II) normalized to unaffected white matter and nCBV(I) was plotted as function of nMTT.

Tumor Segmentation

Using the anatomical MR images, binary glioma ROIs were derived from each MR image slice using an automatic tumor segmentation routine based on knowledge-based Fuzzy c-means (FCM) clustering.

Parametric Image Generation

Applying the two correction methods, parametric leakage maps were generated where $T_1$-dominant and $T_2^*$-dominant leakage constants ($K_2$, Method I or $K_a$, Method II) were rendered with different color palettes (blue colors for positive $T_2^*$-dominant leakage and red colors for negative $T_1$-dominant leakage). Positive and negative $K_2$- and $K_a$ values were identified in the segmented tumor volume and analyzed separately. When differentiating $T_1$- and $T_2^*$-dominant leakage effects, the transfer constants are referred to as $K_a(T_1)$ and $K_a(T_2^*)$ respectively for $T_1$- and $T_2^*$-dominant effects.

All image processing methods, except for the tumor segmentation method were performed using a modified version of nordicICE (NordicImagingLab AS, Bergen, Norway). Tumor segmentation was performed in Matlab R2007a (MathWorks, Natick, US).

Statistical Comparisons

Group differences between HGG and LGG for the derived hemodynamic parameters were tested using Mann-Whitney U-test with a significance level of 0.01. Using normalized histogram peak values derived from the corrected CBV values from tumor segments, logistic regression was used in combination with available survival data to derive Kaplan-Meier survival curves with respect to separating a 'high-risk group' (survival<1 year after MRI exam) from a 'low-risk group' (survival>1 year) regardless of histopathological grading. Statistical analysis was performed using SPSS 17 (SPSS, Inc., Chicago, Ill., USA).

Results

Simulations

Figure 6A:
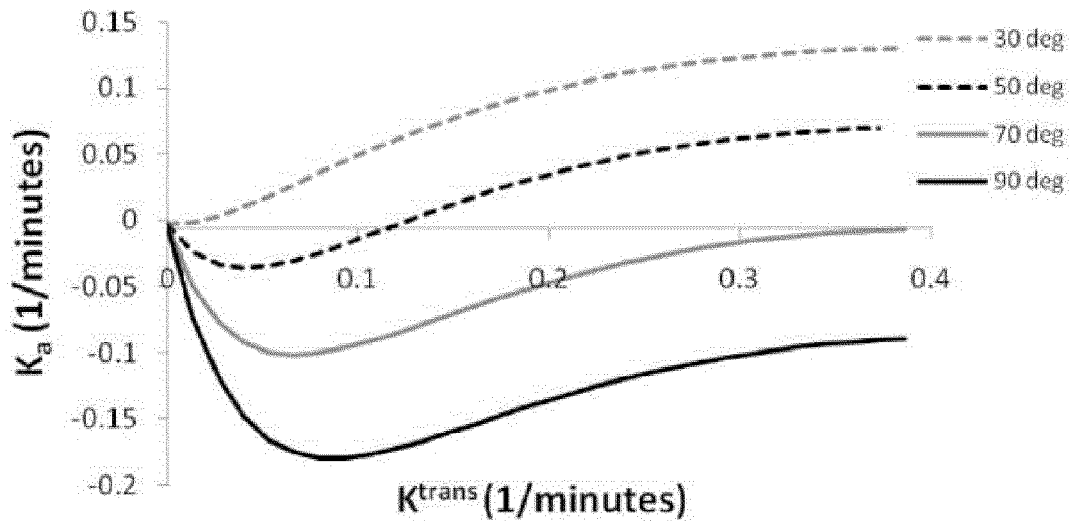
FIGS. 6A-C show the results of the simulation of the correlation between $K_a$ and $K^{trans}$ as function of flip angle (6A), extra-vascular transverse relaxivity ($r2_{ev}$) (6B) and presence or absence of pre-dose (6C).
Figure 6B:
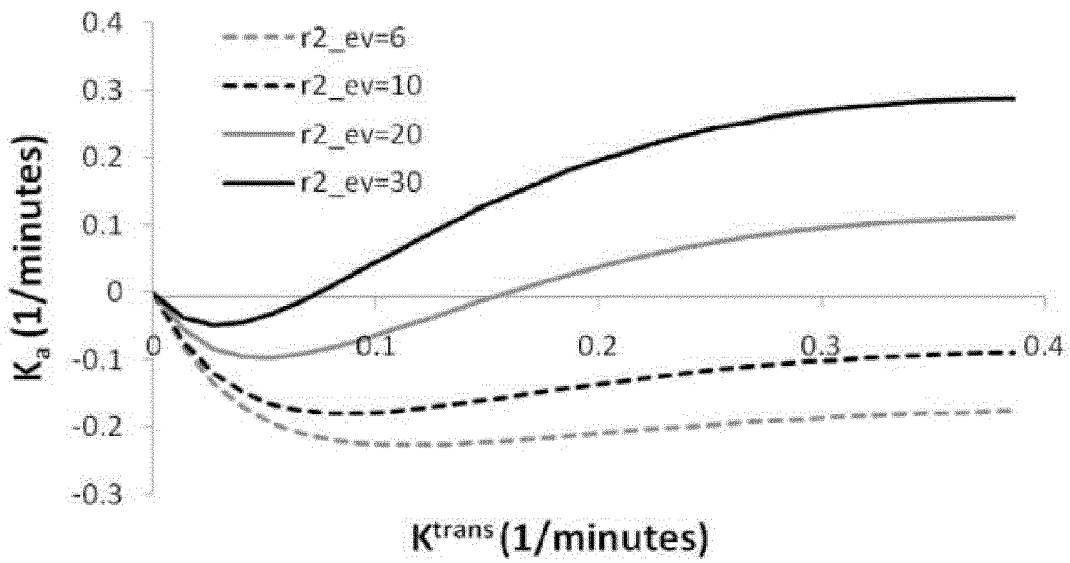
Figure 6C:
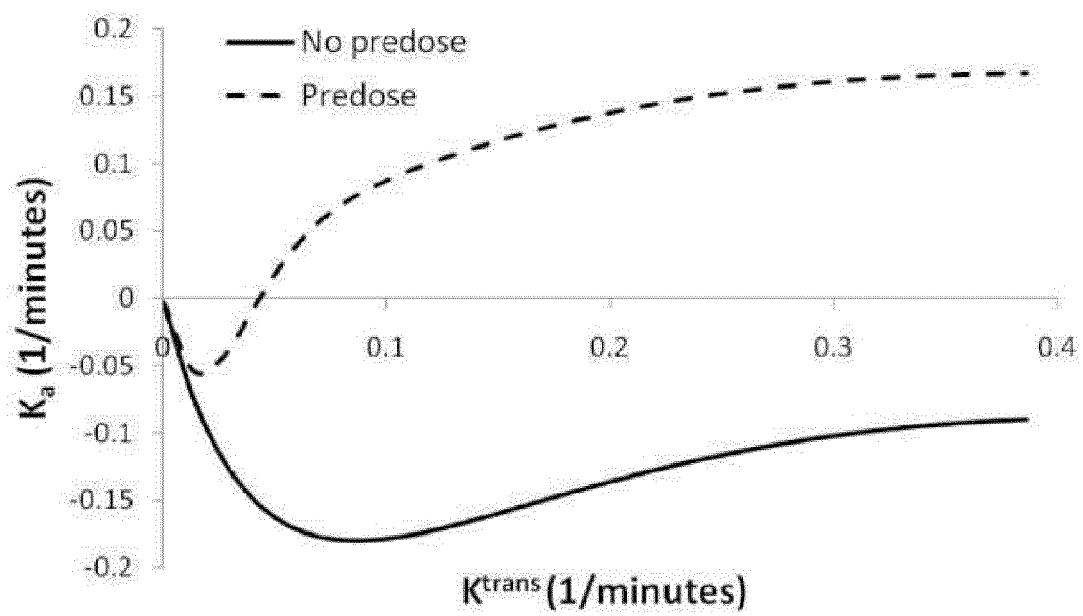

FIGS. 6A-C show the results of the simulation of the correlation between $K_a$ and $K^{trans}$ as function of flip angle (6A), extra-vascular transverse relaxivity ($r2_{ev}$) (6B) and presence or absence of pre-dose (6C). $K_a$ was generally found to be a non-linear function of $K^{trans}$. At low values of $K^{trans}$ and $r2_{ev}$, combined with large flip angles, $K_a$ was initially negatively related to $K^{trans}$ due to a $T_1$-dominant leakage effect. At higher $K^{trans}$ values, $K_a$ was almost independent of $K^{trans}$ for low values of $r2_{ev}$. With increasing $r2_{ev}$ and reduction in flip angle, $K_a$ became increasingly positive ($T_2^*$ dominant leakage) and was a positive function of $K^{trans}$. Use of pre-dose resulted in mainly $T_2^*$-dominant leakage effects and, expect for an initial negative dip, $K_a$ being a positive function of $K^{trans}$ even for high flip angles and low $r2_{ev}$ values.

FIGS. 7A and B show the correlations between the estimated CBV and MTT after extravasation correction using the two correction methods compared to actual- and uncorrected values. Method II was able to reproduce the reference values after correction for both perfusion metrics, whereas Method I resulted in an increasing under-estimation of CBV and MTT with increasing MTT and CBV values. Uncorrected CBV and MTT values were significantly over-estimated for $T_2^*$-dominant leakage (FIG. 7A) and under-estimated for $T_1$-dominant leakage (FIG. 7B). CBF was not significantly affected by extravasation effects (data not shown).

Figure 8A:
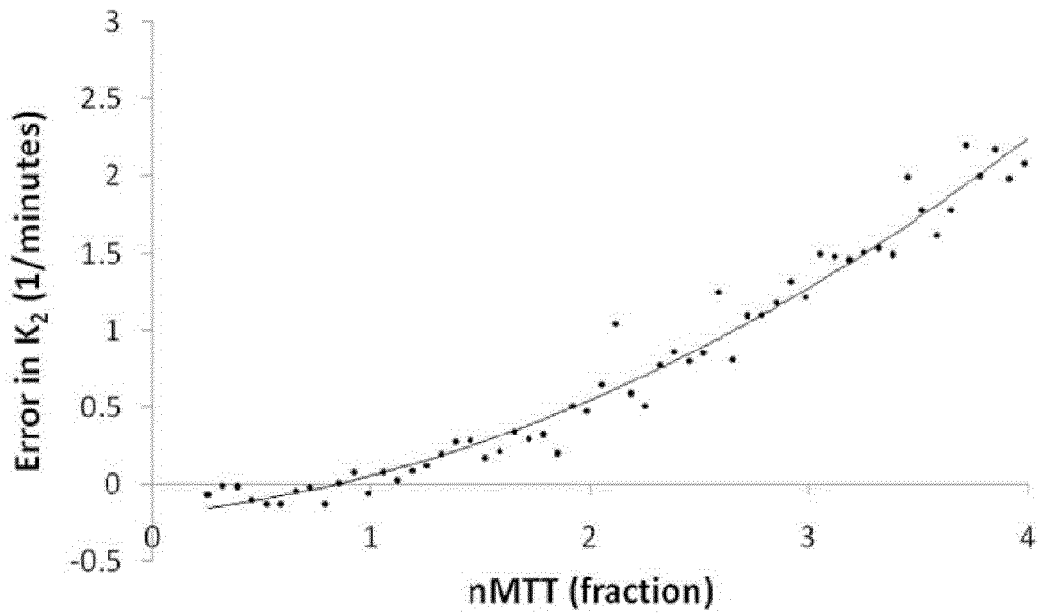
FIGS. 8A and B show the simulated error in $K_2$ ($\Delta K_2$) as a function of nMTT (8A) and the corresponding error in rCBV ($\Delta$rCBV) in percent after correction using Method I (8B) in the situation of no CA extravasation (E=0).

FIGS. 8A and B show the simulated error in $K_2$ ($\Delta K_2$) as a function of nMTT (8A) and the corresponding error in rCBV ($\Delta$rCBV) in percent after correction using Method I (8B) in the situation of no CA extravasation (E=0). $\Delta K_2$ increased quadratically with increasing nMTT and nMTT>1 resulted in a linear increase in the relative under-estimation in rCBV due to an artificially positive value of $K_2$. The error for nMTT<1 was small for both rCBV and $K_2$.

Patient Data

Figure 9A:
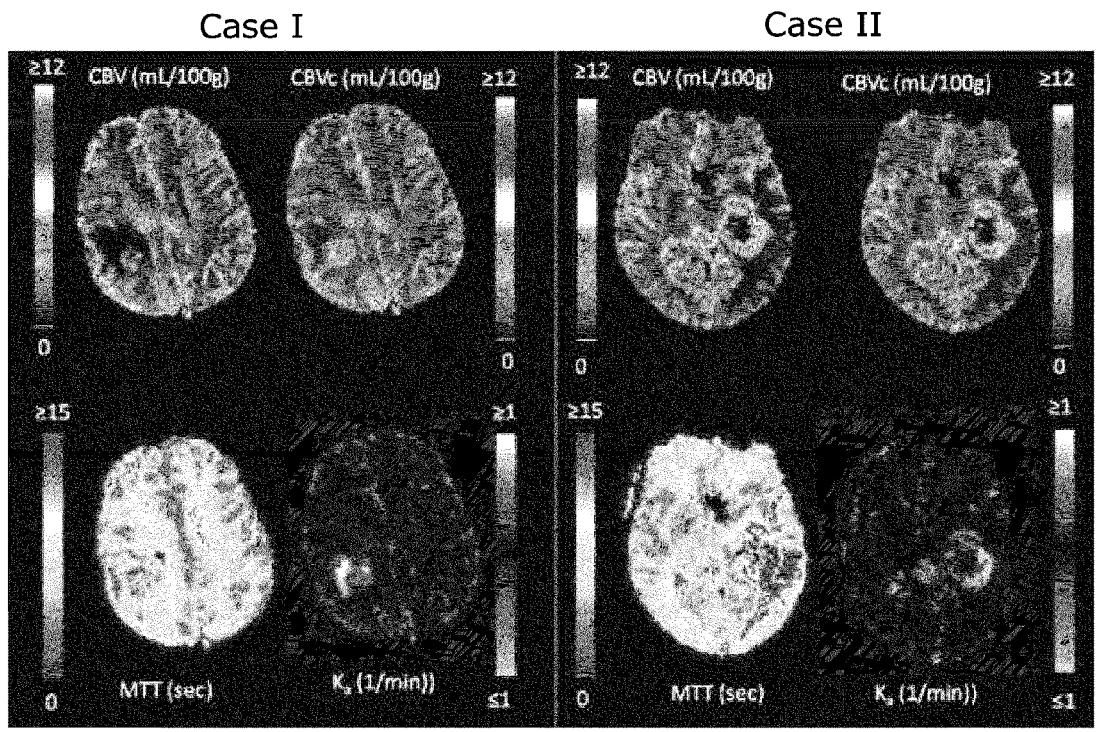
FIG. 9A shows two glioblastoma cases demonstrating $T_1$-dominant (left) and $T_2$*-dominant extravasation effects.
Figure 9B:
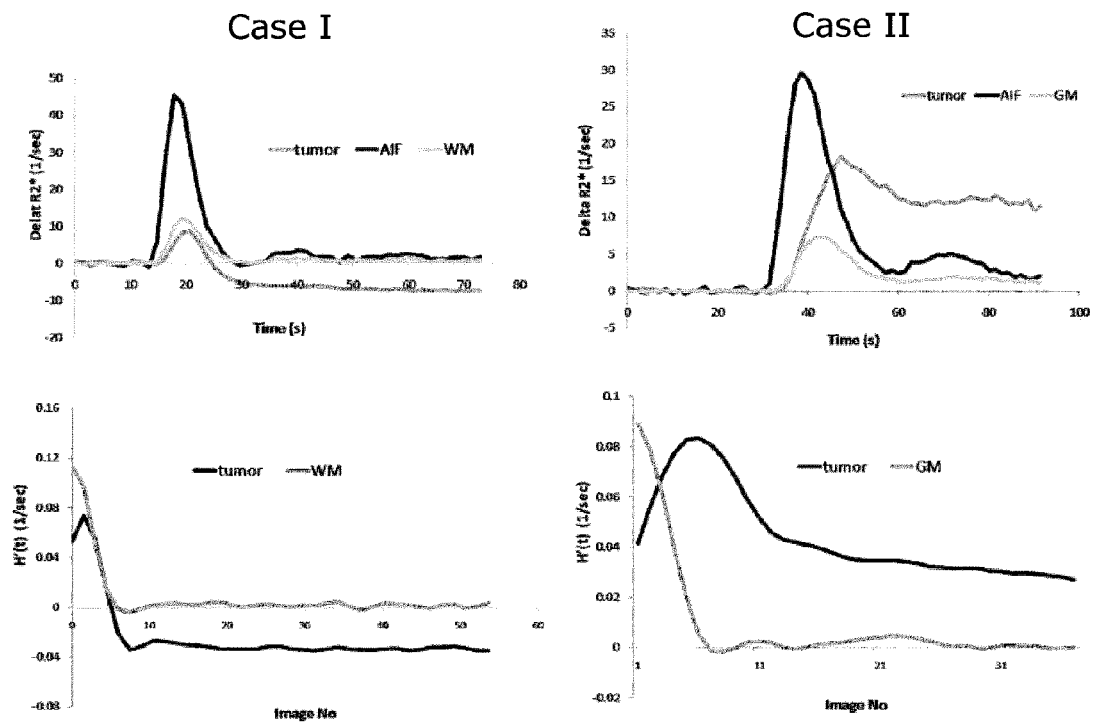
FIG. 9B shows the corresponding dose-response curves and residue functions for the same two sample cases.

About 60% of all tumors with detectable CA extravasation exhibited predominantly $T_1$-enhancing leakage effects (defined as >70% of tumor voxels with non-zero $K_a$ having $K_a$<0). About 10% of the tumors exhibited predominantly $T_2^*$-enhancing leakage and the remaining 30% had an approximately equal mix of T1- and $T_2^*$-dominant leakage effects. FIG. 9A shows two/glioblastoma cases demonstrating $T_1$-dominant (left) and $T_2^*$-dominant extravasation effects. FIG. 9B shows the corresponding dose-response curves and residue functions for the same two sample cases. As predicted by theory and simulations, the $T_1$-dominant leakage resulted in a negative tail in the residue function and $T_2^*$-dominant leakage resulted in a positive tail.

Figure 10:
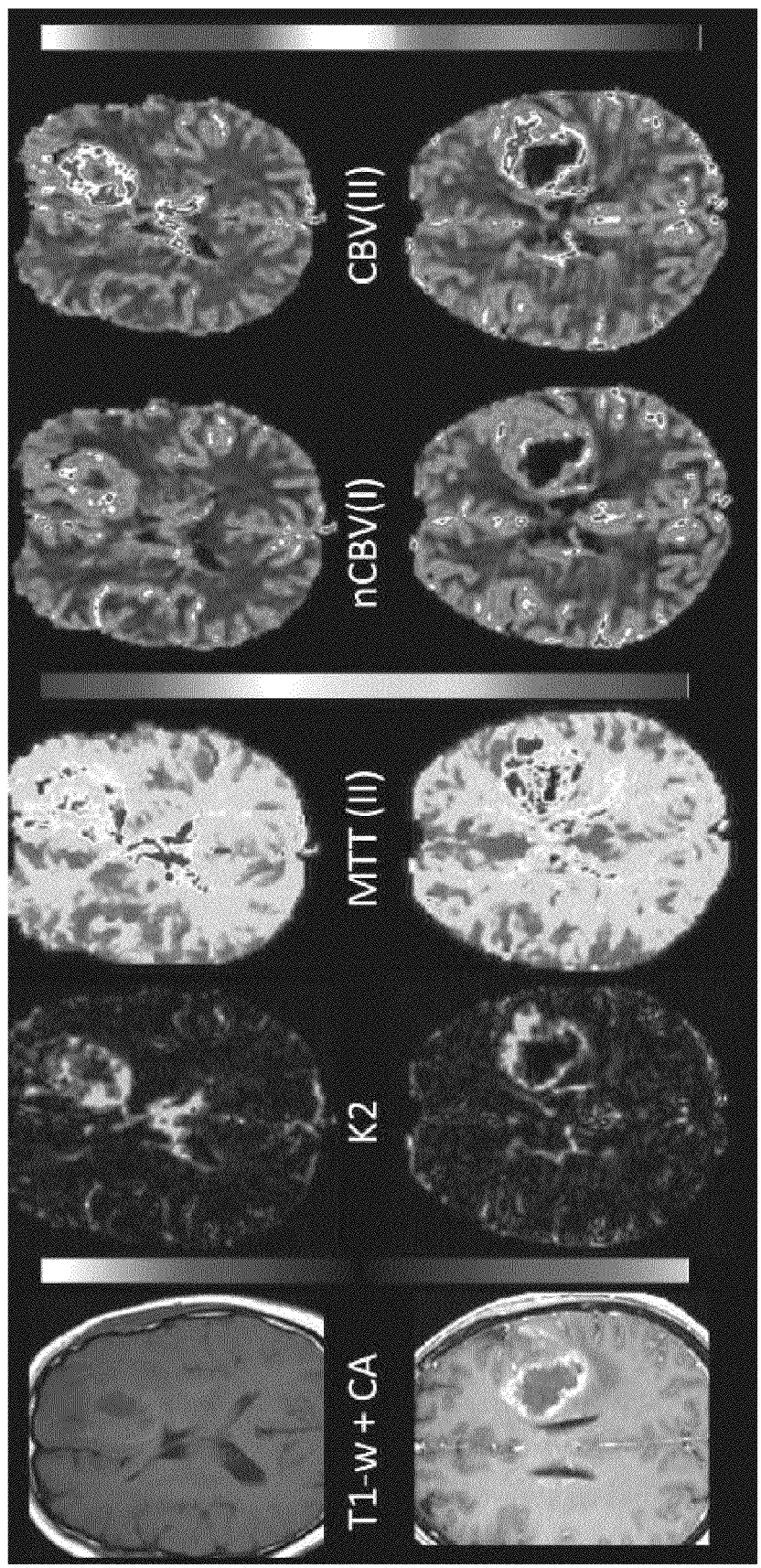
FIG. 10 shows two selected sample cases (upper/lower row) demonstrating the effect of elevated tumor MTT values.

Two selected sample cases demonstrating the effect of elevated tumor MTT values are shown in FIG. 10. The top row shows a grade III anaplastic astrocytoma with significant elevation of nMTT in tumor resulting in apparent $T_2^*$-dominant leakage as seen in the $K_2$-map in spite of absence of visible contrast enhancement in the $T_1$-weighted image after CA administration. The artificial $T_2^*$-dominant leakage resulted in lower nCBV in tumor compared to CBV obtained with Method II. The bottom row shows a glioblastoma with elevated MTT values in the tumor rim resulting in over-estimation of $K_2$ and under-estimation of nCBV in areas of elevated MTT values.

Figure 8B:
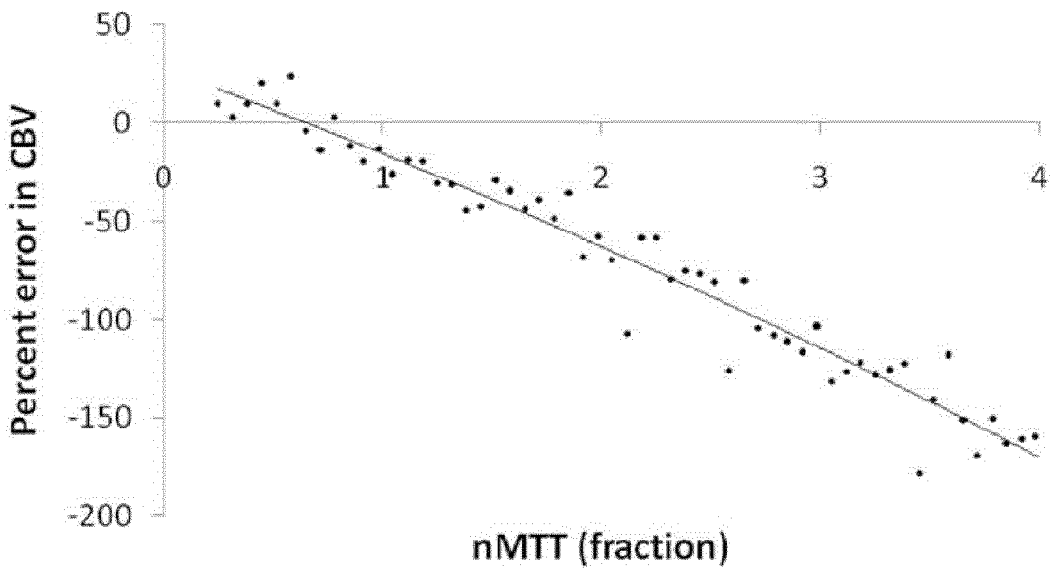
Figure 11:
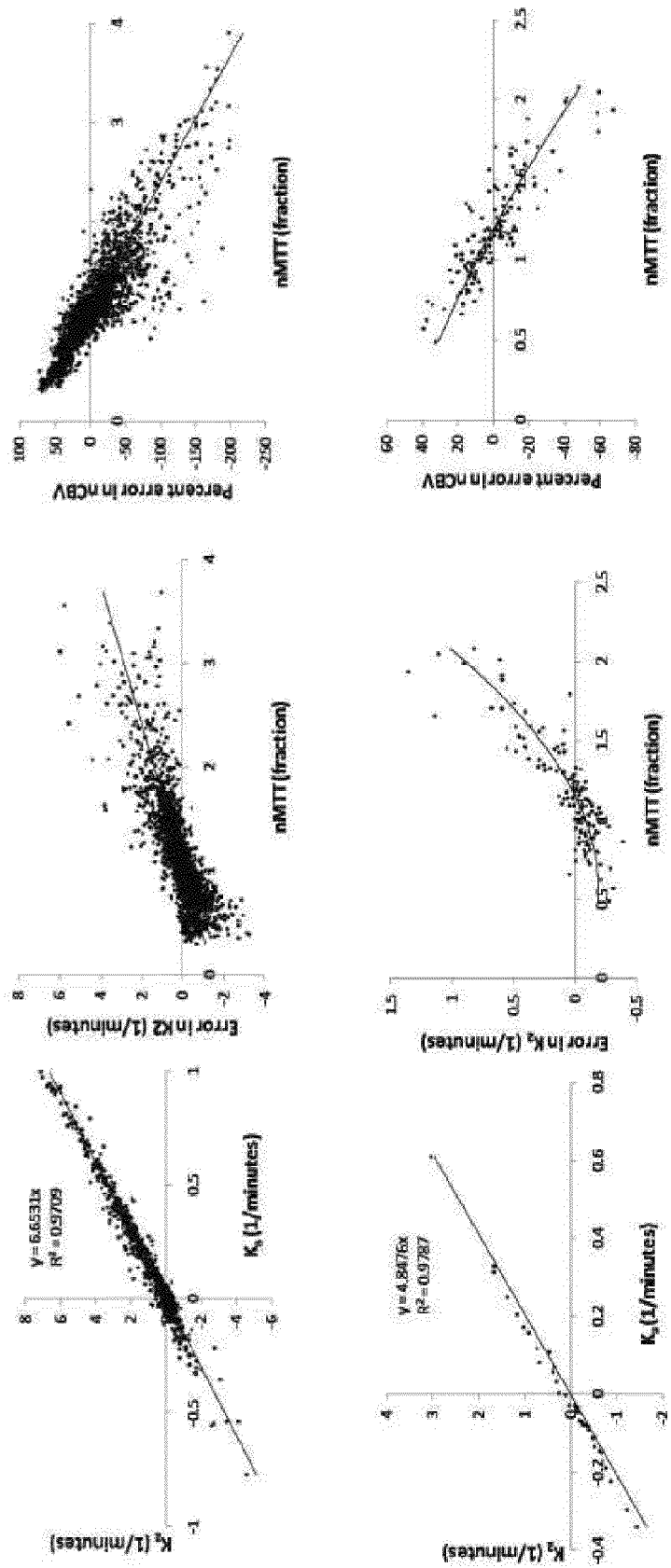
FIGS. 11A-C show pixel-wise analysis of error in $K_2$ and rCBV as function of nMTT for two clinical cases selected based on the presence of a large range of nMTT values in tumor.

FIGS. 11A-C show pixel-wise analysis of error in $K_2$ and rCBV as function of nMTT for two cases selected based on the presence of a large range of nMTT values in tumor. The left column (11A) shows the correlation between $K_a$ and $K_2$ for all pixels with 0.9<nMTT<1.1. A significant and similar linear correlation was observed between $K_a$ and $K_2$ for voxels with nMTT≈1 in both cases and the regression coefficients could therefore be used to determine the residual error in $K_2$ as a function of nMTT. Both cases showed an increase in $\Delta K_2$ (centre column, 11B) and a negative increase in percent difference between nCBV(I) and nCBV(II) (right column, 11C) with increasing nMTT. $\Delta K_2$ had zero crossing at about nMTT=1, in good agreement with simulations (FIGS. 8A-B).

Figure 12:
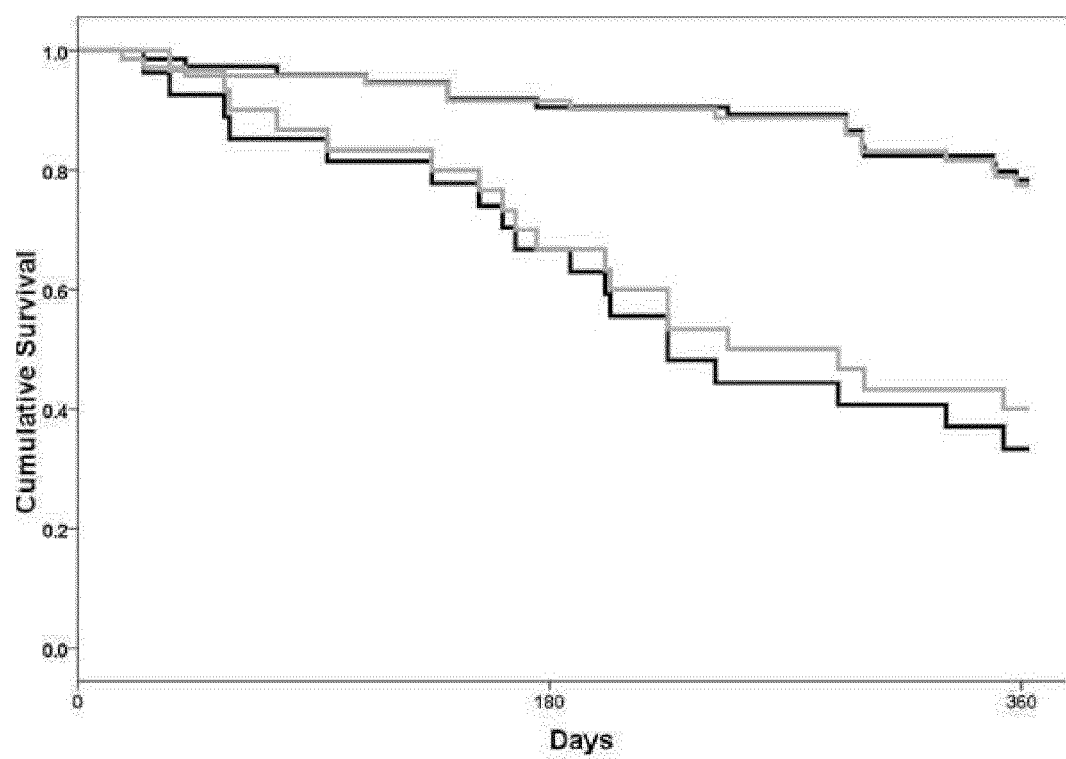
FIG. 12 shows Kaplan-Meier survival curves.

The mean leakage corrected whole tumor CBV (+/−SD) was 2.1±0.8 mL/100 g and 3.9±1.7 mL/100 g, respectively in LGG and HGG (P<0.001). Using the same correction method, both mean MTT and $K_a(T_2^*)$ was significantly higher (P<0.001) in HGG compared to LGG. The average MTT in HGG was 5.6±1.5 s and 4.0±1.0 s in LGG. Mean $K_a(T_2^*)$ was 0.17±0.08 min$^{-1}$ in HGG and 0.11±0.08 min$^{-1}$ in LGG. $K_a(T_1)$ was not significantly different in HGG and LGG. The $K_a$ values obtained in vivo were in the same range as those obtained in the simulations (FIGS. 6A-C). For the Kaplan-Meier analysis, the log-rank (Mantel-Cox Chi-Square) values describing the difference between the low- and high-risk survival curves were higher for correction Method II than for Method I (23.69; P<0.001 and 16.46; P<0.001, respectively). The Kaplan-Meier survival curves are shown in FIG. 12.

The above method enables estimation of CA extravasation and multiple perfusion metrics directly from the tissue residue function. The development of the method was motivated by limitations in existing methodology and an identified need for quantitative assessment of tumor hemodynamic properties. Although a post processing based method for leakage correction is established (Boxerman et al. 2006), two important limitations of this reference correction method were identified: 1) the method is sensitive to deviations in tumor MTT compare to reference tissue MTT and 2) the method only corrects for $T_1$-dominant leakage. The latter point can easily be overcome by allowing the apparent transfer constant ($K_2$) to assume both positive and negative values. The MTT sensitivity is, however, inherent in the method and we show through simulations and in patient data that elevated MTT in tumor tissue may lead to underestimation of rCBV as a result of incorrect estimation of $K_2$. Given that MTT was found to be significantly higher in HGG than in LGG, our results suggest that the reference method may underestimate rCBV in tumors even when leakage correction is performed. The proposed correction method providing absolute leakage corrected CBV values was found to provide improved survival prediction compared to the reference correction method of Boxerman et al applied to normalized CBV values. The survival analysis was based on whole tumor CBV histogram analysis, an approach previously shown to robustly predict outcome from automatically generated tumor ROIs.

The problem of MTT sensitivity of the reference method has previously been pointed out by other investigators. Quarles et al (Quarles et al. 2005) proposed an alternative MIT insensitive correction method which also relies on AIF deconvolution. Different from the method of Quarles et al we aimed at estimating all hemodynamic parameters directly from the leakage corrected tissue residue function, thereby avoiding the step of re-generating a leakage corrected tissue response curve. Although no gold standard currently exists, alternative models providing combined assessment of both perfusion and CA extravasation have been proposed.

The model assumptions used in the correction method discussed here deviates somewhat from the model presented previously where capillary perfusion and EV leakage were assumed to occur as two parallel processes originating from the same arterial source. Although the current model probably better describes the underlying kinetics of the CA the estimation of $K_a$ is in practice identical for the two models and the CBV correction differs only by the non-zero offset value $N_c$ (Equation 32) in the modified model.

The proposed method relies on accurate estimation of the tissue residue function which requires both robust estimation of the AIF and stable deconvolution in the presence of noise. Given the recent advent of automated AIF detection methods (see e.g. Mouridsen et al. 2006), it is expected that much of the current user-dependence in associated with AIF determination can be eliminated. The need of the method to identify a 'steady-state' level in a noisy and generally oscillating residue function is also a challenge. We minimized oscillations by employing an iterative Tikhonov regularization based SVD deconvolution method and were able to obtain robust estimates of both $T_1$-dominant and $T_2$*-dominant leakage effects using this approach.

Computer simulations were used to investigate the relationship between the measured apparent rate constant $K_a$ and $K^{trans}$. Although the performed simulations make several simplifying assumptions regarding in vivo relaxation effects, the results clearly suggest that the apparent transfer constant estimated from DSC-MRI is generally not linearly related to the underlying permeability surface area product of the tumor tissue, even when extravasation is permeability limited (CBF>>PS). This lack of linear correlation is partly due to the complex relationship between CA concentration in tissue and the measured change signal intensity and corresponding transformation to apparent transverse relaxation rates. The presence of both $T_1$- and $T_2$*-relaxation effects in the EES can result in both positive and negative apparent rate constants depending on the underlying tissue properties as well as sequence parameters. The presence of both these effect was confirmed in the patient data. An additional source of non-linearity is due to the assumption of negligible CA reflux. For the higher $K^{trans}$ values tested in these simulations the required condition that $K^{trans}T_N/v_e \ll 1$ is clearly violated, resulting in an under-estimation of $K_a$ at high $K^{trans}$ values. An improved model where the tail of H(t) is not assumed to be a constant but is fitted to the full exponential function (Equation 29) is therefore warranted and may provide a better estimate of $K^{trans}$. However, even with improved kinetic models, absolute estimations of $K^{trans}$ from DSC acquisitions will remain challenging due to an unpredictable- and generally non-linear dose response in DSC-MRI.

The simulations confirmed that the use of a pre-dose reduces $T_1$-effects and gives predominantly positive $K_a$ values except at very low $K^{trans}$ where an initial negative 'dip' was observed. The presence of this initial 'inverted' $K_a$ response at low $K^{trans}$ values could be a potential challenge but this effect needs to be confirmed in clinical data where a pre-dose is used. In the current study no pre-dosing and a large flip angle of 90 deg was used, both factors resulting in an increased sensitive to $T_1$-dominant leakage effects. Although $K_a$ should be expected to correlate with tumor grade, such a correlation was only observed for $K_a(T_2^*)$. The lack of correlation of $K_a(T_1)$ with tumor grade may be due to the non-linear dependence, and to a certain degree the non-dependence of $K_a(T_1)$ and ($K_a<0$) on $K^{trans}$, as seen in FIGS. 4A and 4B. Given the results of the simulations showing that transition from $T_1$- to $T_2$*-dominant leakage depends strongly on the effective transverse relaxivity in the EES, it could be hypothesized that the presence or absence of the two competing leakage effects may convey relevant information concerning the extra-vascular tissue structure within the tumor. This effect could thus be a potential marker for assessment of treatment response by for instance monitoring of changes in the relative $K_a(T_1)/K_a(T_2^*)$ fraction during treatment. This observation warrants further investigation.

In summary, the presented extravasation correction method enables robust correction for both $T_1$- and $T_2$*-dominant leakage effects independent of the MTT of the target tissue. The method can be combined with automated methods for AIF detection, providing estimates of multiple hemodynamic parameters without, user interaction.

Although the present invention has been described in connection with the specified embodiments, it should not be construed as being in any way limited to the presented examples. The scope of the present invention is to be interpreted in the light of the accompanying claim set. In the context of the claims, the terms "comprising" or "comprises" do not exclude other possible elements or step. Also, the mentioning of references such as "a" or "an" etc. should not be construed as excluding a plurality. In general, and specifically in the claims, "or" should be interpreted as a non-exclusive or. The use of reference signs in the claims with respect to elements indicated in the figures shall also not be construed as limiting the scope of the invention. Furthermore, individual features mentioned in different claims, may possibly be advantageously combined, and the mentioning of these features in different claims does not exclude that a combination of features is not possible and advantageous.

REFERENCES

Boxerman J L, Schmainda K M, Weisskoff R M (2006) Relative cerebral blood volume maps corrected for contrast agent extravasation significantly correlate with glioma tumor grade, whereas uncorrected maps do not. *AJNR Am J Neuroradiol* 27:859-867

U.S. Pat. No. 6,807,441

Quarles C C, Ward B D, Schmainda K M (2005) Improving the reliability of obtaining tumor hemodynamic parameters in the presence of contrast agent extravasation. *Magn Reson Med* 53:1307-1316

U.S. Pat. No. 7,567,832

Mouridsen K, Christensen S, Gyldensted L, Ostergaard L (2006) Automatic selection of arterial input function using cluster analysis. *Magn Reson Med* 55:524-531

Bjornerud A, Emblem K E (2010) A fully automated method for quantitative cerebral hemodynamic analysis using DSC-MRI. *J Cereb Blood Flow Metab* 30:1066-1078.

The invention claimed is:

1. A method for estimating contrast agent extravasation in contrast agent based perfusion imaging methods to be performed by an electronic processor, the method comprising:
   accessing perfusion image data comprising a signal related to contrast agent concentration as a function of time in a voxel during the first and consecutive passages of the contrast agent through the vascular system;
   representing the signal by a convolution, $R_{ps}'(t) \otimes C_p'(t)$, of an apparent residue function, $R_{ps}'(t)$, and an estimated contrast agent concentration in plasma, $C_p'(t)$, and determining the apparent residue function $R_{ps}'(t)$ by deconvolution of the signal with $C_p'(t)$;
   estimating a first leakage rate constant $K_a$ from a tail part of the apparent residue function, where $K_a$ is quantifying an apparent rate of contrast agent extravasation from plasma to extravascular, extracellular space (EES);
   determining an extravasation corrected residue function, $R_{corr}(t)$, from the apparent residue function $R_{ps}'(t)$ and the estimated $K_a$, wherein the extravasation corrected residue function, $R_{corr}(t)$, is determined using at least one of the following algorithms:

$$R_{corr}(t) = R_{ps}'(t) - K_a$$

$$R_{corr}(t) = 1/F(R_{ps}'(t) - K_a(1 - k_{ep}t))$$

$$R_{corr}(t) = 1/F(R_{ps}'(t) - K_a e^{-k_{ep}t})$$

$$R_{corr}(t) = 1/F(R_{ps}'(t) - \text{mean}[R_{ps}'(t > t_{tp})]);$$

where F is the tissue flow and $t_{tp}$ is an estimated start time of the tail part and where $k_{ep}$ is a second leakage rate constant which is quantifying an apparent rate of contrast agent reflux from tissue back to blood.

2. A method for estimating contrast agent extravasation in contrast agent based perfusion imaging methods to be performed by an electronic processor, the method comprising:
   accessing perfusion image data comprising a signal related to contrast agent concentration as a function of time in a voxel during the first and consecutive passages of the contrast agent through the vascular system;
   representing the signal by a convolution, $R_{ps}'(t) \otimes C_p'(t)$, of an apparent residue function, $R_{ps}'(t)$, and an estimated contrast agent concentration in plasma, $C_p'(t)$, and determining the apparent residue function $R_{ps}'(t)$ by deconvolution of the signal with $C_p'(t)$;
   estimating a first leakage rate constant $K_a$ from a tail part of the apparent residue function, where $K_a$ is quantifying an apparent rate of contrast agent extravasation from plasma to extravascular, extracellular space (EES),
   wherein the tail part of the apparent residue function is determined by one or more of:
      fitting a singly peaked, monotonously decreasing function, L(t), with zero asymptotes to a global maxima peak of the apparent residue function and defining the tail part of the apparent residue function as the part where the amplitude of the apparent residue function is consistently larger than the amplitude of L(t);
      estimating the approximate mean transit time (MTT) from the perfusion image data, and from this estimate, estimating a time, $t_{tp}$, larger than MTT and using R'(t) for $t > t_{tp}$ as the tail part of the apparent residue function;
      finding the section of the apparent residue function following its peak amplitude with minimum relative variance (variance divided by mean value) over a predefined section length.

3. A method for estimating contrast agent extravasation in contrast agent based perfusion imaging methods to be performed by an electronic processor, the method comprising:
   accessing perfusion image data comprising a signal related to contrast agent concentration as a function of time in a voxel during the first and consecutive passages of the contrast agent through the vascular system;
   representing the signal by a convolution, $R_{ps}'(t) \otimes C_p'(t)$, of an apparent residue function, $R_{ps}'(t)$, and an estimated contrast agent concentration in plasma, $C_p'(t)$, and determining the apparent residue function $R_{ps}'(t)$ by deconvolution of the signal with $C_p'(t)$;
   estimating a first leakage rate constant $K_a$ from a tail part of the apparent residue function, where $K_a$ is quantifying an apparent rate of contrast agent extravasation from plasma to extravascular, extracellular space (EES); and
   wherein $K_a$ is estimated as being proportional to a mean value of the tail part of the apparent residue function.

4. A method for estimating contrast agent extravasation in contrast agent based perfusion imaging methods to be performed by an electronic processor, the method comprising:
   accessing perfusion image data comprising a signal related to contrast agent concentration as a function of time in a voxel during the first and consecutive passages of the contrast agent through the vascular system;
   representing the signal by a convolution, $R_{ps}'(t) \otimes C_{ps}'(t)$, of an apparent residue function, $R_{ps}'(t)$, and an estimated contrast agent concentration in plasma, $C_p'(t)$, and determining the apparent residue function $R_{ps}'(t)$ by deconvolution of the signal with $C_p'(t)$;
   estimating a first leakage rate constant $K_a$ from a tail part of the apparent residue function, where $K_a$ is quantifying an apparent rate of contrast agent extravasation from plasma to extravascular, extracellular space (EES); and
   wherein $K_a$ is estimated as being proportional to an asymptote of the apparent residue function.

5. A method according to claim 1, for estimating contrast agent extravasation in contrast agent based perfusion imaging methods to be performed by an electronic processor, the method comprising:
   accessing perfusion image data comprising a signal related to contrast agent concentration as a function of time in a voxel during the first and consecutive passages of the contrast agent through the vascular system;
   representing the signal by a convolution, $R_{ps}'(t) \otimes C_p'(t)$, of an apparent residue function, $R_{ps}'(t)$, and an estimated contrast agent concentration in plasma, $C_p'(t)$, and determining the apparent residue function $R_{ps}'(t)$ by deconvolution of the signal with $C_p'(t)$;
   estimating a first leakage rate constant $K_a$ from a tail part of the apparent residue function, where $K_a$ is quantifying an apparent rate of contrast agent extravasation from plasma to extravascular, extracellular space (EES); and
   wherein the estimation comprises fitting an exponential or linear function involving $K_a$ as a constant to at least the tail part of the apparent residue function.

6. A method for estimating contrast agent extravasation in contrast agent based perfusion imaging methods to be performed by an electronic processor, the method comprising:
   accessing perfusion image data comprising a signal related to contrast agent concentration as a function of time in a voxel during the first and consecutive passages of the contrast agent through the vascular system;
   representing the signal by a convolution, $R_{ps}'(t) \otimes C_p'(t)$, of an apparent residue function, $R_{ps}'(t)$, and an estimated contrast agent concentration in plasma, $C_p'(t)$, and determining the apparent residue function $R_{ps}'(t)$ by deconvolution of the signal with $C_p'(t)$;

estimating a first leakage rate constant $K_a$ from a tail part of the apparent residue function, where $K_a$ is quantifying an apparent rate of contrast agent extravasation from plasma to extravascular, extracellular space (EES); and wherein the estimation further comprises estimating a second leakage rate constant $k_{ep}$ quantifying an apparent rate of contrast agent reflux EES back to plasma based on the tail part of the apparent residue function.

7. A method for estimating contrast agent extravasation in contrast agent based perfusion imaging methods to be performed by an electronic processor, the method comprising:

accessing perfusion image data comprising a signal related to contrast agent concentration as a function of time in a voxel during the first and consecutive passages of the contrast agent through the vascular system;

representing the signal by a convolution, $R_{ps}'(t) \otimes C_p'(t)$, of an apparent residue function, $R_{ps}'(t)$, and an estimated contrast agent concentration in plasma, $C_p'(t)$, and determining the apparent residue function $R_{ps}'(t)$ by deconvolution of the signal with $C_p'(t)$;

estimating a first leakage rate constant $K_a$ from a tail part of the apparent residue function, where $K_a$ is quantifying an apparent rate of contrast agent extravasation from plasma to extravascular, extracellular space (EES); and an automated segmentation of imaged tissue into a tumor region and white and/or grey matter, and wherein a mean value of $K_a$ are estimated for the tumor region and for the white and/or grey matter.

8. A method for estimating contrast agent extravasation in contrast agent based perfusion imaging methods to be performed by an electronic processor, the method comprising:

accessing perfusion image data comprising a signal related to contrast agent concentration as a function of time in a voxel during the first and consecutive passages of the contrast agent through the vascular system;

representing the signal by a convolution, $R'(t) \otimes C_p'(t)$, of an apparent residue function, $R_{ps}'(t)$, and an estimated contrast agent concentration in plasma, $C_p'(t)$, and determining the apparent residue function $R_{ps}'(t)$ by deconvolution of the signal with $C_p'(t)$;

estimating a first leakage rate constant $K_a$ from a tail part of the apparent residue function, where $K_a$ is quantifying an apparent rate of contrast agent extravasation from plasma to extravascular, extracellular space (EES); and wherein $K_a$ is allowed to take both positive and negative values, and wherein the method further comprises separating between $T_1$- and $T_2^*$-dominant leakage by determining the sign of $K_a$, so that negative $K_a$ values reflect $T_1$-dominant leakage effects and positive $K_a$ values reflect $T_2^*$-dominant leakage effects.

9. A method for estimating contrast agent extravasation in contrast agent based perfusion imaging methods to be performed by an electronic processor, the method comprising:

accessing perfusion image data comprising a signal related to contrast agent concentration as a function of time in a voxel during the first and consecutive passages of the contrast agent through the vascular system;

representing the signal by a convolution, $R_{ps}'(t) \otimes C_p'(t)$, of an apparent residue function, $R_{ps}'(t)$, and an estimated contrast agent concentration in plasma, $C_p'(t)$, and determining the apparent residue function $R_{ps}'(t)$ by deconvolution of the signal with $C_p'(t)$;

estimating a first leakage rate constant $K_a$ from a tail part of the apparent residue function, where $K_a$ is quantifying an apparent rate of contrast agent extravasation from plasma to extravascular, extracellular space (EES); and wherein the apparent residue function, $R_{ps}'(t)$, is estimated as:

$$R_{ps}'(t) = R_{ps}(t) + e = F \begin{bmatrix} R(t_0) \\ R(t_1) \\ \vdots \\ R(t_{N-1}) \end{bmatrix} + K_a \begin{bmatrix} e^{-k_{ep}t_0} \\ e^{-k_{ep}t_1} \\ \vdots \\ e^{-k_{ep}t_{N-1}} \end{bmatrix}$$

where e is an error term due to leakage, R(t) is a tissue specific residue function, F is proportional to tissue flow, N is a number of data-points, and $k_{ep}$ is a rate constant from the EES to the intravascular space.

10. A method for estimating contrast agent extravasation in contrast agent based perfusion imaging methods to be performed by an electronic processor, the method comprising:

accessing perfusion image data comprising a signal related to contrast agent concentration as a function of time in a voxel during the first and consecutive passages of the contrast agent through the vascular system;

representing the signal by a convolution, $R_{ps}'(t) \otimes C_p'(t)$, of an apparent residue function, $R_{ps}'(t)$, and an estimated contrast agent concentration in plasma, $C_p'(t)$, and determining the apparent residue function $R_{ps}'(t)$ by deconvolution of the signal with $C_p'(t)$;

estimating a first leakage rate constant $K_a$ from a tail part of the apparent residue function, where $K_a$ is quantifying an apparent rate of contrast agent extravasation from plasma to extravascular, extracellular space (EES); and wherein the apparent residue function, $R_{ps}'(t)$, is estimated as:

$$R_{ps}'(t) = R_{ps}(t) + e = F \begin{bmatrix} 1 \\ R(t_1) \\ \vdots \\ R(t_C) \\ 0 \\ 0 \\ \vdots \\ 0 \end{bmatrix} + K_a \begin{bmatrix} 0 \\ 0 \\ \vdots \\ 0 \\ 1 \\ \exp(-K^{trans}\Delta t/v_e) \\ \vdots \\ \exp(-K^{trans}N\Delta t/v_e) \end{bmatrix}$$

where e is an error term due to leakage, R(t) is a tissue specific residue function, F is proportional to tissue flow, $\Delta t$ is a sampling interval, N is a number of data-points, $t_c$ is a time index corresponding to a capillary transit time of the CA, $T_c$, $K^{trans}$ is a transfer constant describing the CA flux from the IVS to the EES, and $v_e$ is a leakage space per unit volume.

11. A method for estimating contrast agent extravasation in contrast agent based perfusion imaging methods to be performed by an electronic processor, the method comprising:

accessing perfusion image data comprising a signal related to contrast agent concentration as a function of time in a voxel during the first and consecutive passages of the contrast agent through the vascular system;

representing the signal by a convolution, $R_{ps}'(t) \otimes C_p'(t)$, of an apparent residue function, $R_{ps}'(t)$, and an estimated contrast agent concentration in plasma, $C_p'(t)$, and determining the apparent residue function $R_{ps}'(t)$ by deconvolution of the signal with $C_p'(t)$;

estimating a first leakage rate constant $K_a$ from a tail part of the apparent residue function, where $K_a$ is quantifying an apparent rate of contrast agent extravasation from plasma to extravascular, extracellular space (EES); and estimating a factor to be used in correction of partial volume (PV) effects in contrast agent based perfusion MR or CT images to be performed by an electronic processor, the method comprising determining a PV correction factor, $f_{pv}$, as a ratio between parts of the signal following the first passage of the contrast agent from one or more voxels comprising arterial blood and one or more voxels filled with venous blood, respectively.

12. A method of distinguishing between $T_1$-dominant and $T_2^*$-dominant extravasation effects in perfusion imaging to be performed by an electronic processor, the method comprising:

accessing perfusion image data comprising a signal related to contrast agent concentration as a function of time in a voxel during the first and consecutive passages of the contrast agent through the vascular system;

representing the signal by a convolution, $R_{ps}'(t) \otimes C_p'(t)$, of an apparent residue function, $R_{ps}'(t)$, and an estimated contrast agent concentration in plasma, $C_p'(t)$, and determining the apparent residue function $R_{ps}'(t)$ for each voxel by deconvolution of the signal with $C_p'(t)$;

determining a sign of the tail part of the apparent residue function; and generating an image of a parameter reflecting the determined sign and magnitude.

13. An automated method for DSC-MRI comprising the following to be performed by an electronic processor for at least each slice in acquired image data:

automatic detection of an arterial input function (AIF);

estimating a first leakage rate constant $K_a$ quantifying an apparent rate of contrast agent extravasation and a partial volume correction factor, $f_{pv}$, according to claim 7.

* * * * *